US011279951B2

(12) United States Patent
Brough et al.

(10) Patent No.: US 11,279,951 B2
(45) Date of Patent: Mar. 22, 2022

(54) ADENOVIRAL VECTOR ENCODING HUMAN ATONAL HOMOLOG-1 (HATH1)

(71) Applicant: GenVec, Inc., Gaithersburg, MD (US)

(72) Inventors: Douglas E. Brough, Gaithersburg, MD (US); Damodar R. Ettyreddy, Clarksburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 1035 days.

(21) Appl. No.: 15/933,689

(22) Filed: Mar. 23, 2018

(65) Prior Publication Data

US 2018/0208944 A1 Jul. 26, 2018

Related U.S. Application Data

(62) Division of application No. 14/879,318, filed on Oct. 9, 2015, now Pat. No. 9,951,351.

(60) Provisional application No. 62/061,748, filed on Oct. 9, 2014.

(51) Int. Cl.
*C12N 15/861* (2006.01)
*C12N 15/86* (2006.01)
*A61K 38/16* (2006.01)
*A61K 48/00* (2006.01)

(52) U.S. Cl.
CPC .............. *C12N 15/86* (2013.01); *A61K 38/16* (2013.01); *A61K 48/0058* (2013.01); *A61K 48/0075* (2013.01); *A61K 48/00* (2013.01); *C12N 2710/10043* (2013.01); *C12N 2710/10343* (2013.01); *C12N 2830/008* (2013.01)

(58) Field of Classification Search
CPC .......... C12N 15/86; C12N 2710/10343; C12N 2830/008; C12N 2710/10043; A61K 38/16; A61K 48/0058; A61K 48/0075; A61K 48/00; A61P 43/00; A61P 27/16; A61P 27/02; A61P 27/00
See application file for complete search history.

(56) References Cited

U.S. PATENT DOCUMENTS

| | | |
|---|---|---|
| 4,797,368 A | 1/1989 | Carter et al. |
| 5,543,328 A | 8/1996 | McClelland et al. |
| 5,559,099 A | 9/1996 | Wickham et al. |
| 5,712,136 A | 1/1998 | Wickham et al. |
| 5,731,190 A | 3/1998 | Wickham et al. |
| 5,756,086 A | 5/1998 | McClelland et al. |
| 5,770,442 A | 6/1998 | Wickham et al. |
| 5,770,580 A | 6/1998 | Ledley et al. |
| 5,792,751 A | 8/1998 | Ledley et al. |
| 5,801,030 A | 9/1998 | McVey et al. |
| 5,804,413 A | 9/1998 | DeLuca |
| 5,837,511 A | 11/1998 | Falck-Pedersen et al. |
| 5,837,532 A | 11/1998 | Preston et al. |
| 5,837,681 A | 11/1998 | Magal |
| 5,840,686 A | 11/1998 | Chader et al. |
| 5,846,782 A | 12/1998 | Wickham et al. |
| 5,849,561 A | 12/1998 | Falck-Pedersen |
| 5,849,572 A | 12/1998 | Glorioso et al. |
| 5,851,806 A | 12/1998 | Kovesdi et al. |
| 5,871,727 A | 2/1999 | Curiel |
| 5,885,808 A | 3/1999 | Spooner et al. |
| 5,922,315 A | 7/1999 | Roy |
| 5,929,041 A | 7/1999 | Magal |
| 5,962,311 A | 10/1999 | Wickham et al. |
| 5,965,358 A | 10/1999 | Carrión et al. |
| 5,965,541 A | 10/1999 | Wickham et al. |
| 5,994,106 A | 11/1999 | Kovesdi et al. |
| 5,994,128 A | 11/1999 | Fallaux et al. |
| 6,033,908 A | 3/2000 | Bout et al. |
| 6,057,155 A | 5/2000 | Wickham et al. |
| 6,063,627 A | 5/2000 | McVey et al. |
| 6,127,525 A | 10/2000 | Crystal et al. |
| 6,153,435 A | 11/2000 | Crystal et al. |
| 6,165,754 A | 12/2000 | Crystal et al. |
| 6,168,941 B1 | 1/2001 | Liu et al. |
| 6,225,113 B1 | 5/2001 | Brough et al. |
| 6,228,646 B1 | 5/2001 | Hardy |
| 6,329,190 B1 | 12/2001 | Wickham et al. |
| 6,329,200 B1 | 12/2001 | McVey et al. |
| 6,358,507 B1 | 3/2002 | Kaplan et al. |
| 6,383,795 B1 | 5/2002 | Carrión et al. |
| 6,440,728 B1 | 8/2002 | McVey et al. |
| 6,447,995 B1 | 9/2002 | Carrión et al. |
| 6,455,314 B1 | 9/2002 | Wickham et al. |
| 6,465,253 B1 | 10/2002 | Wickham et al. |
| 6,475,757 B2 | 11/2002 | McVey et al. |
| 6,482,616 B1 | 11/2002 | Kovesdi et al. |

(Continued)

FOREIGN PATENT DOCUMENTS

| | | |
|---|---|---|
| EP | 0613945 A2 | 9/1994 |
| EP | 1203819 A2 | 5/2002 |

(Continued)

OTHER PUBLICATIONS

U.S. Appl. No. 14/879,318, filed Oct. 9, 2015.

(Continued)

*Primary Examiner* — Titilayo Moloye

(74) *Attorney, Agent, or Firm* — Leydig, Voit, & Mayer, Ltd.

(57) ABSTRACT

The invention is directed to a replication-deficient adenoviral vector comprising a nucleic acid sequence encoding a human atonal homolog-1 (Hath1) protein operably linked to a human glial fibrillary acidic protein (GFAP) promoter. The invention also is directed to a composition and method utilizing the adenoviral vector to generate sensory cells in the inner ear of a human.

8 Claims, 2 Drawing Sheets

Specification includes a Sequence Listing.

(56) References Cited

U.S. PATENT DOCUMENTS

| | | | |
|---|---|---|---|
| 6,576,456 | B2 | 6/2003 | Wickham et al. |
| 6,649,373 | B2 | 11/2003 | Brough et al. |
| 6,660,521 | B2 | 12/2003 | Brough et al. |
| 6,821,775 | B1 | 11/2004 | Kovesdi et al. |
| 6,838,444 | B1 | 1/2005 | Zoghbi et al. |
| 6,913,922 | B1 | 7/2005 | Bout et al. |
| 7,053,200 | B1 | 5/2006 | Zoghbi et al. |
| 7,442,688 | B2 | 10/2008 | Zoghbi et al. |
| 7,470,673 | B2 | 12/2008 | Zoghbi et al. |
| 2001/0043922 | A1 | 11/2001 | Kovesdi et al. |
| 2001/0047081 | A1 | 11/2001 | Roelvink et al. |
| 2002/0004040 | A1 | 1/2002 | Kovesdi et al. |
| 2002/0031831 | A1 | 3/2002 | Kovesdi et al. |
| 2002/0034735 | A1 | 3/2002 | Carrión et al. |
| 2002/0099024 | A1 | 7/2002 | Wickham et al. |
| 2002/0110545 | A1 | 8/2002 | Kovesdi et al. |
| 2002/0151027 | A1 | 10/2002 | Wickham et al. |
| 2002/0192665 | A1 | 12/2002 | Zoghbi et al. |
| 2003/0099619 | A1 | 5/2003 | Wickham et al. |
| 2004/0166091 | A1 | 8/2004 | Brough |
| 2007/0141029 | A1 | 6/2007 | Brough |
| 2009/0041759 | A1 | 2/2009 | McVey et al. |
| 2012/0316226 | A1 | 12/2012 | Brough |
| 2014/0005257 | A1 | 1/2014 | Brough |

FOREIGN PATENT DOCUMENTS

| | | |
|---|---|---|
| JP | 2002-330786 A | 11/2002 |
| WO | WO 91/02788 A1 | 3/1991 |
| WO | WO 93/24529 A1 | 12/1993 |
| WO | WO 95/19182 A1 | 7/1995 |
| WO | WO 95/34671 A1 | 12/1995 |
| WO | WO 96/04394 A1 | 2/1996 |
| WO | WO 96/07734 A2 | 3/1996 |
| WO | WO 96/26281 A1 | 8/1996 |
| WO | WO 97/00326 A1 | 1/1997 |
| WO | WO 97/09439 A | 3/1997 |
| WO | WO 97/12986 A2 | 4/1997 |
| WO | WO 97/17983 A1 | 5/1997 |
| WO | WO 97/20051 A2 | 6/1997 |
| WO | WO 97/21826 A2 | 6/1997 |
| WO | WO 97/30722 A1 | 8/1997 |
| WO | WO 98/00014 A1 | 1/1998 |
| WO | WO 98/07865 A1 | 2/1998 |
| WO | WO 98/07877 A1 | 2/1998 |
| WO | WO 98/13048 A1 | 4/1998 |
| WO | WO 98/15637 A1 | 4/1998 |
| WO | WO 98/19700 A1 | 5/1998 |
| WO | WO 98/40509 A1 | 9/1998 |
| WO | WO 98/53087 A1 | 11/1998 |
| WO | WO 98/54346 A1 | 12/1998 |
| WO | WO 98/56937 A2 | 12/1998 |
| WO | WO 99/04806 A1 | 2/1999 |
| WO | WO 99/06064 A1 | 2/1999 |
| WO | WO 99/06583 A1 | 2/1999 |
| WO | WO 99/15686 A1 | 4/1999 |
| WO | WO 99/42088 A2 | 8/1999 |
| WO | WO 99/54441 A1 | 10/1999 |
| WO | WO 00/00628 A1 | 1/2000 |
| WO | WO 00/12765 A1 | 3/2000 |
| WO | WO 00/15823 A1 | 3/2000 |
| WO | WO 00/23084 A1 | 4/2000 |
| WO | WO 00/27426 A1 | 5/2000 |
| WO | WO 00/34444 A2 | 6/2000 |
| WO | WO 00/34496 A2 | 6/2000 |
| WO | WO 00/73764 A2 | 12/2000 |
| WO | WO 01/58494 A2 | 8/2001 |
| WO | WO 01/58940 A2 | 8/2001 |
| WO | WO 01/77304 A1 | 10/2001 |
| WO | WO 01/92549 A2 | 12/2001 |
| WO | WO 02/29388 A2 | 4/2002 |
| WO | WO 2004/076626 A2 | 9/2004 |
| WO | WO 2014/039908 A1 | 3/2014 |

OTHER PUBLICATIONS

"Balance Disorders," http://www.nidcd.nih.gov/health/balance/pages/balance_disorders.aspx, accessed Mar. 4, 2015.
"NIH Hearing loss," http://www.nlm.nih.gov/medlineplus/ency/article/001045.htm, accessed Mar. 11, 2015.
Akazawa et al., "A mammalian helix-loop-helix factor structurally related to the product of Drosophila proneural gene atonal is a positive transcriptional regulator expressed in the developing nervous system," The Journal of Biological Chemistry, 270(15): 8730-8738 (Apr. 14, 1995).
Avraham et al., "Prospects for gene therapy in hearing loss," J. Basic Clin. Physiol. Pharmacol. (Israel), 14 (2): 77-83 (2003).
Baker et al., "Repair of the vestibular system via adenovector delivery of Atoh1: a potential treatment for balance disorders," Advances in Otorhinolaryngology, 66:52-63 (Feb. 2009).
Baylor College of Medicine, "MATH1 signal heralds process of differentiation in intestinal lining," Biocompare News, Dec. 6, 2001. (Retrieved from the internet on Dec. 10, 2001.).
Ben-Arie et al., "Abnormal cerebellar development in mice lacking the murine homolog of the Drosphila proneural gene atonal," Am. J. Hum. Genet., 59 (4 Suppl.): A46 (Abstract #232) (1996).
Ben-Arie et al., "Evolutionary conservation of sequence and expression of the bHLH protein Atonal suggests a conserved role in neurogenesis," Hum. Mol. Genet., 5 (9), 1207-1216 (1996).
Ben-Arie et al., "Math 1 is essential for genesis of cerebellar granule neurons," Nature, 390: 169-172 (Nov. 13, 1997).
Ben-Arie et al., "Functional conservation of atonal and Math1 in the CNS and PNS," Development, 127: 1039-1048 (2000).
Bergelson et al., "Isolation of a common reception for Coxsackie B viruses and adenoviruses 2 and 5," Science, 275 (5304): 1320-3 (1997).
Bermingham et al., "Math1: An essential gene for the generation of inner ear hair cells," Science, 284: 1837-1841 (Jun. 11, 1999).
Bermingham-McDonogh, "Hair cell regeneration: winging our way towards a sound future," Curr. Opin. Neurobiol., 13: 119-126 (2003).
Bork, "Powers and pitfalls in sequence analysis: The 70% Hurdle," Genome Research, 10: 398-400 (2000).
Brake et al., "Human adenovirus-vectored foot-and-mouth disease vaccines: establishment of a vaccine produce profile through in vitro testing," Developments in Biologicals, 134:123-133 (Aug. 2012).
Brockmeier et al., "Adenovirus-mediated expression of interferon-alpha delays viral replication and reduces disease signs in swine challenged with porcine reproductive and respiratory syndrome virus," Viral Immunology, 22(3):173-80 (Jun. 2009).
Brockmeier et al., "The presence of alpha interferon at the time of infection alters the innate and adaptive immune responses to porcine reproductive and respiratory syndrome virus," Clinical Vaccine Immunology, 19(4):508-14 (Apr. 2012).
Brough et al., "Activation of transgene expression by early region 4 is responsible for a high level of persistent transgene expression from adenovirus vectors in vivo," J. Virol., 71 (12): 9206-9213 (Dec. 1997).
Brown et al., "Math5 encodes a murine basic helix-loop-helix transcription factor expressed during early states of retinal neurogenesis," Development, 725: 4821-4833 (Nov. 9, 1998).
Bruder et al., "Identification of a Suppressor Mutation That Improves the Yields of Hexon-Modified Adenovirus Vectors," Journal of Virology, 87(17):9661-71 (Sep. 2013).
Butman et al., "Comprehensive Characterization of the 293-ORF6 Cell Line," Developments in Biologicals, 123:225-33 (2003).
Carey et al., "Hair cell regeneration and recovery of the vestibuloocular reflex in the avian vestibular system," J. Neurophysiol., 76 (5): 3301-3312 (Nov. 1996).
Carswell et al., "Efficiency of utilization of the simian vius 40 late polyadenylation site: effects of upstream sequences," Mol. Cell Biol., 9 (10), 4248-4258 (1989).
Chader, "Multipotential differentiation of human Y-79 retinoblastoma cells in attachment culture," Cell Different., 20 (2-3): 209-216 (1987).

(56) References Cited

OTHER PUBLICATIONS

Chen et al., "The role of Math1 in inner ear development: Uncoupling the establishment of the sensory primordium from hair cell fate determination," *Development*, 129 (10): 2495-2505 (2002).
Chen et al., "Persistent expression of PEDF in the eye using high-capacity adenovectors," *Molecular Therapy*, 16(12):1986-94 (Dec. 2008).
Chien et al., "Neuronal type information encoded in the basic-helix-loop-helix domain of proneural genes," *Proc. Natl. Acad. Sci. U.S.A.*, 93 (23), 13239-13244 (1996).
Crawford-Miksza et al., "Analysis of 15 Adenovirus hexon proteins reveals the location and structure of seven hypervariable regions containing serotype-specific residues," *J. Virol.*, 70(3): 1836-1844 (1996).
Crea et al., "Chemical synthesis of genes for human insulin," *Proc. Natl. Acad. Sci. USA*, 75 (12): 5765-5769 (Dec. 1978).
Crystal, "Transfer of Genes to Humans: Early Lessons and Obstacles to Success," *Science*, 270 (5235): 404-410 (Oct. 20, 1995).
Deonarain, "Ligand-targeted receptor-mediated vectors for gene delivery," *Expert Opin. Ther. Pat.*, 8(1): 53-69 (1998).
Devarajan et al., "Adenovector-mediated gene delivery to human umbilical cord mesenchymal stromal cells induces inner ear cell phenotype," *Cell. Reprogram.*, 15 (1), 43-54 (2013).
Dharmapuri et al., "Engineered adenovirus serotypes for overcoming anti-vector immunity," *Expert Opn. Biol. Ther.*, 9 (10), 1279-1287 (2009).
Dooling, "Recovery of hearing and vocal behavior after hair-cell regeneration," *Proc. Natl. Acad. Sci. USA*, 94: 14206-14210 (Dec. 1997).
Eberl, "Feeling the vibes: chordotonal mechanisms in insect hearing," *Current Opinion in Neurobiology*, 9 (4): 389-93 (Aug. 1999).
Einfeld et al., "Reducing the native tropism of adenovirus vectors requires removal of both CAR and integrin interactions," *J. Virol.*, 75 (23): 11284-11291 (Dec. 2001).
Ford et al., "Protein transduction: an alternative to genetic intervention?" *Gene Therapy*, 8: 1-4 (2002).
Forge et al., "The molecular architecture of the inner ear," *British Medical Bulletin*, 63: 5-24 (2002).
Gall et al., "Rescue and production of vaccine and therapeutic adenovirus vectors expressing inhibitory transgenes," *Molecular Biotechnology*, 35(3):263-73 (Mar. 2007).
Gassner et al., "Canalostomy as a surgical approach for cochlear gene therapy in the rat," *Anatomical Record*, 295(11):1830-6 (Nov. 2012).
GENBANK Accession No. AAB41305.1 (dated Jan. 24, 1997).
GENBANK Accession No. U61148 (dated Jan. 25, 1997).
Graham et al., "Characteristics of a human cell line transformed by DNA from human adenovirus type 5," *J. Gen. Virol.*, 36: 59-72 (1977).
Groves et al., "The genetics of hair cell development and regeneration," *Annu. Rev. Neurosci.*, 36, 361-381 (2013).
Guo et al., "The nuclear matrix protein NMP-1 is the transcription factor YY1" *Proc. Natl. Acad. Sci. USA*, 92: 10526-10530 (1995).
Hamilton et al., "Alternate serotype adenovector provides long-term therapeutic gene expression in the eye," *Molecular Vision*, 14:2535-46 (Dec. 30, 2008).
Hamilton et al., "Repeated administration of adenovector in the eye results in efficient gene delivery," *Investigative Ophthalmology and Visual Science*, 47(1):299-305 (Jan. 2006).
Hassan et al., "Atonal regulates neurite arborization but does not act as a proneural gene in the *Drosophila* brain," *Neuron*, 25: 549-561 (Mar. 2000).
Hassan et al., "Doing the math: is the mouse a good model for fly development?" *Genes and Development*, 14: 1852-1865 (2000).
Hasson et al. "Expression in cochlea and retina of myosin VIIa, the gene product defective in Usher syndrome type 1B," *Proc. Natl. Acad. Sci. USA*, 92: 9815-9819 (Oct. 1995).
Hawkins, "Comparative otopathology: aging, noise, and ototoxic drugs," *Adv. Otorhinolaryngol.*, 20: 125-141 (1973).

Heller et al., "Molecular markers for cell types of the inner ear and candidate genes for hearing disorders," *Proc. Natl. Acad. Sci. USA*, 95:11400-11405 (1998).
Ho et al., "Synthetic Protein Transduction Domains: Enhanced Transduction Potential in Vitro and in Vivo," *Cancer Research*, 61: 474-477 (Jan. 15, 2001).
Holt et al., "Functional expression of exogenous proteins in mammalian sensory hair cells infected with adenoviral vectors," *Neurophysiology*, 81 (4): 1881-8 (1999).
Iizuka et al., "Noninvasive In Vitro Delivery of Transgene via Adeno-Associated Virus into Supporting Cells of the Neonatal Mouse Cochlea," *Human Gene Therapy*, 19 (4): 384-390 (Apr. 2008).
International Search Report, Application No. PCT/US2015/054836, dated Dec. 18, 2015.
Itakura et al., "Expression in *Escherichia coli* of a chemically synthesized gene for the hormone somatostatin," *Science*, 198 (4321): 1056-1063 (1977).
Izumikawa et al., "Auditory hair cell replacement and hearing improvement by Atoh1 gene therapy in deaf mammals," *Nature Medicine*, 11: 271-276 (Feb. 13, 2005).
Jarman et al., "Atonal is a proneural gene that directs chordotonal organ formation in the *Drosophila* peripheral nervous system," *Cell*, 73:1307-1321 (Jul. 2, 1993).
Jarman et al., "Atonal is the proneural gene for *Drosophila* photoreceptors," *Nature*, 369: 398-400 (Jun. 2, 1994).
Jero et al., "Cochlear gene delivery through an intact round window membrane in mouse," *Hum. Gene Ther.*, 12: 539-548 (Mar. 20, 2001).
Jero et al., "A surgical approach appropriate for targeted cochlear gene therapy in the mouse," *Hearing Research*, 151: 106-114 (2001).
Kanzaki et al., "From gene identification to gene therapy," *Audiol. Neurootol.*, 7 (3): 161-164 (2002).
Kawamoto et al., "Math1 gene transfer generates new cochlear hair cells in mature guinea pigs in vivo," *J. Neurosci.*, 23 (11): 4395-4400 (Jun. 1, 2003).
Kawamoto et al., "The functional and structural outcome of inner ear gene transfer via the vestibular and cochlear fluids in mice," *Mol. Ther.*, 4 (6): 575-585 (2001).
Kiernan et al., "Sox2 is required for sensory organ development in the mammalian inner ear," *Nature*, 434 (7036): 1031-5 (Feb. 2005).
Kim et al., "XATH-1, a vertebrate homolog of *Drosophila* atonal, induces neuronal differentiation with ectodermal progenitors," *Developmental Biology*, Article D8978572, 187: 1-12 (1997).
Klickstein, "CGF166 Atonal Gene Therapy for Hearing Loss & Vestibular Dysfunction: Review of NIH OBA protocol #1310-1260," CGF166, *RAC Meeting*, Novartis, 1-16 (Dec. 4, 2013).
Konishi et al., "Gene transfer into guinea pig cochlea using adeno-associated virus vectors," *J. Gene Med.*, 10 (6): 610-618 (2008).
Koup et al., "Replication-defective adenovirus vectors with multiple deletions do not induce measurable vector-specific T cells in human trials," *Journal of Virology*, 83(12):6318-22 (Jun. 2009).
Kraft et al., "Atoh1 induces auditory hair cell recovery in mice after ototoxic injury," *Laryngoscope*, 123(4):992-9, Author Manuscript (Apr. 2013).
Kwun et al., "Immunohistochemical localization of urea transporters A and B in the rat cochlea," *Hearing Research*, 183 (1-2): 84-96 (2003).
Lalwani et al., "Expression of Adeno-Associated Virus Integrated Transgene Within the Mammalian Vestibular Organs," *Am. J. Otol.*, 19: 390-395 (1998).
Lalwani et al., "In Vitro and In Vivo Assessment of the Ability of Adeno-Associated Virus-Brain Derived Neurotropic Factor to Enhance Spiral Ganglion Cell Survival Following Ototoxic Insult," *The Laryngoscope*, 112 (8): 1325-1334 (Aug. 2002).
Laughlin et al., "Closing of infectious adeno-associated virus genomes in bacterial plasmids," *Gene*, 23: 65-73 (1983).
Lautermann et al., "Expression of the gap junction connexins 26 and 30 in the rat cochlea," *Cell & Tissue Research*, 294 (3): 415-20 (1998).
Ledley, "Pharmaceutical approach to somatic gene therapy," *Pharmaceutical Research*, 13 (11): 1595-1614 (1996).
Lemiale et al., "Novel adenovirus vaccine vectors based on the enteric-tropic serotype 41 " *Vaccine*, 25(11):2074-84, Author Manuscript (Mar. 2007).

(56) References Cited

OTHER PUBLICATIONS

Lewis et al., "Distinct expression patterns of notch family receptors and ligands during development of the mammalian inner ear," *Mechanisms of Development*, 78(1-2): 159-63 (1998).
Luebke et al., "A modified adenovirus can transfect cochlear hair cells in vivo without compromising cochlear function," *Gene Ther.*, 8: 789-794 (2001).
Luebke et al., "Cochlear function and transgene expression in the guinea pig cochlea, using adenovirus- and adeno-associated virus-directed gene transfer," *Hum. Gene Ther.*, 12: 773-781 (May 1, 2001).
Luebke et al., "Adenoviral and AAV-mediated gene transfer to the inner ear: role of serotype, promoter, and viral load on in vivo and in vitro infection efficiencies," *Adv. Otorhinolaryngol.*, 66: 87-98 (2009).
Marinovic et al., "Ubiquitin (UbC) expression in muscle cells is increased by glucocorticoids through a mechanism involving Sp1 and MEK1*," *J. Biol. Chem.*, 277(19): 16673-16681 (May 10, 2002).
McVey et al., "Adenovirus vector library: an approach to the discovery of gene and protein function," *Journal of General Virology*, 84(Pt 12):3417-22 (Dec. 2003).
McVey et al., "Adenoviruses isolated from wild gorillas are closely related to human species C viruses," *Virology*, 444(1-2):119-23 (Sep. 2013).
McVey et al., "Characterization of human adenovirus 35 and derivation of complex vectors," *Virology Journal*, 7:276 (Oct. 2010).
McVey et al., "Rapid Construction of Adenoviral Viral Vectors by Lambda Phage Genetics," *J. Virol.*, 76(8): 3670-3677 (2002).
McVey et al., "Repeat administration of proteins to the eye with a single intraocular injection of an adenovirus vector," *Molecular Therapy*, 16(8):1444-9 (Aug. 2008).
Millar et al., "Molecular mechanisms regulating hair follicle development," *J. Invest. Dermatol.*, 118: 216-225 (2002).
Miller et al., "Targeted vectors for gene therapy," *FASEB J.*, 9 (2): 190-199 (1995).
Mizguchi et al., "CAR- or alphav inegrin-binding ablated adenovirus vectors, but not fiber-modified vectors containing RGD peptide, do not change the systemic gene transfer properties in mice," *Gene Ther.*, 9 (12): 796-76 (2002).
Montcouquiol et al., "Intracellular signals that control cell proliferation in mammalian balance epithelia: Key roles for phosphatidylinositol-3 kinase, mammalian target of rapamycin, and S6 kinases in preference to calcium, protein kinase C, and mitogen-activated protein kinase," *J. Neurosci.*, 21 (2): 570-580 (Jan. 15, 2001).
Mori et al., "Pigment epithelium-derived factor inhibits retinal and choroidal neovascularization," *J. Cell. Physiol.*, 188: 253-263 (2001).
Morris et al., "A peptide carrier for the delivery of biologically active proteins into mammalian cells," *Nature Biotechnology*, 19: 1173-1176 (Dec. 2001).
Mountain, "Gene therapy: the first decade," *Tibtech*, 18: 119-125 (2000).
Mulvaney et al., "Atoh1, an essential transcription factor in neurogenesis and intestinal and inner ear development: function, regulation, and context dependency," *J. Assoc. Res. Otolaryngol.*, 13 (3), 281-289 (2012).
Pfannenstiel et al., "Bcl-2 gene therapy prevents aminoglycoside-induced degeneration of auditory and vestibular hair cells," *Audiolgy Neurotology*, 14(4):254-66 (2009).
Pignolo et al., "Senescent WI-38 cells fail to express EPC-1, a gene induced in young cells upon entry into the G0 state," *J. Biol. Chem.*, 268 (12): 8949-8957 (Apr. 25, 1993).
Praetorius et al., "Adenovector-mediated hair cell regeneration is affected by promoter type," *Acta Otolaryngol.*, 130 (2), 215-222 (2010).
Praetorius et al., Adenoviral vectors for improved gene delivery to the inner ear, *Hearing Research*, 248(1-2):31-8, Author Manuscript (Feb. 2009).

Praetorius et al., "Pharmacodynamics of adenovector distribution within the inner ear tissues of the mouse," *Hearing Research*, 227(1-2):53-8 (May 2007).
Ramalingam et al., "E1(−)E4(+) adenoviral gene transfer vectors function as a "pro-life" signal to promote survival of primary human endothelial cells," *Blood*, 93(9):2936-44 (May 1, 1999).
Rio et al., "Glial Fibrillary Acidic Protein Expression and Promoter Activity in the Inner Ear of Developing and Adult Mice," *The Journal of Comparative Neurology*, 442:156-162 (2002).
Robbins et al., "Viral vectors for gene therapy," *Pharmacol. Ther.*, 80: 35-47 (1998).
Roy et al., "Circumvention of immunity to the adenovirus major coat protein hexon," *J. Virol.*, 72 (8): 6875-9 (1998).
Ryan et al., "Gene Therapy for the Inner Ear: Challenges and Promises," *Adv. Otorhinolaryngol.*, 66: 1-12 (2009).
Sabaté et al., "Adenovirus for neurodegenerative diseases: in vivo strategies and ex vivo gene therapy using human neural progenitors," *Clin. Neurosci.*, 3: 317-321 (1996).
Saukkonen et al., "Tissue-specific protomers for cancer gene therapy," *Expert Opin. Biol. Ther.*, 4 (5); 683-96 (2004).
Schlecker et al., "Selective atonal gene delivery improves balance function in a mouse model of vestibular disease," *Gene Ther.*, 18(9), 884-890 (2011).
Schutta et al., "Multiple efficacy studies of an adenovirus-vectored foot-and-mouth disease virus serotype A24 subunit vaccine in cattle using homologous challenge," *Vaccine*, 34(27): 3214-20 (Jun. 8, 2016).
Schwab et al., "Neuronal Basic Helix-Loop-Helix Proteins (NEX, neuroD, NDRF): Spatiotemporal Expression and Targeted Disruption of the NEX Gene in Transgenic Mice," *J. of Neuroscience*, 18 (4): 1408-1418 (Feb. 15, 1998).
Schwarze et al., "In vivo protein transduction: delivery of a biologically active protein in the mouse," *Science*, 285: 1569-1572 (Sep. 3, 1999).
Sherman et al., "HIV-1 Vpr Displays Natural Protein-Transducing Properties: Implications for Viral Pathogenesis," *Virology*, 302: 95-105 (2002).
Shou et al., "Robust generation of new hair cells in the mature mammalian inner ear by adenoviral expression of Hath1," *Mol. Cell. Neurosci.*, 23 (2), 169-179 (2003).
Staecker et al., "Brain-derived neurotrophic factor gene therapy prevents spiral ganglion degeneration after hair cell loss," *Otolaryngol. Head Neck Surg.*, 119:7-13 (1998).
Staecker et al., "Gene expression in the mammalian cochlea: a study of multiple vector systems," *Acta Otolaryngol.*, 121:157-163 (2001).
Staecker et al., "Development of gene therapy for inner ear disease: Using bilateral vestibular hypofunction as a vehicle for translational research," *Hearing Research*, 276(1-2):44-5, Author Manuscript (Jun. 2011).
Staecker et al., "Drug delivery to the inner ear using gene therapy," *Otolaryngology Clinics of North America*, 37(5):1091-108 (Oct. 2004).
Staecker et al., "Optimizing atoh1-induced vestibular hair cell regeneration," *Laryngoscope*, 124 (Suppl 5):S1-S12, Author Manuscript (Oct. 2014).
Staecker et al., "Vestibular hair cell regeneration and restoration of balance function induced by math1 gene transfer," *Otol. Neurotol.*, 28 (2): 223-31 (2007).
Stone et al., "New serotypes of adenoviral vectors," *Curr. Opin. Mol. Ther.*, 8 (5): 423-31 (2006).
Stöver et al., "Cochlear gene transfer: round window versus cochleostomy inoculation," *Hearing Res.*, 136: 124-130 (1999).
Sun et al., "Transcriptional regulation of atonal during development in the *Drosophila* peripheral nervous system," *Development*, 125: 3731-3740 (1998).
Suzuki et al., "Effect of transgenic GDNF expression of gentamicin-induced cochlearand vestibular toxicity," *Gene Ther.*, 7 (12): 1046-1054 (Jun. 2000).
Takumi et al., "Select types of supporting cell in the inner ear express aquaporin-4 water channel protein," *European Journal of Neuroscience*, 10 (12) : 3584-95 (1998).

(56) References Cited

OTHER PUBLICATIONS

Thibodeau et al., "Sense of Hearing and Balance: The Ear," Unit 3 Communication, Control and Integration, *Anatomy and Physiology*, 4th Ed., pp. 454-455, Mosby Inc., St. Louis, MO, USA (1999).
Tong et al., "Expression patterns of the JEM-1 gene in normal and tumor cells: ubiquity contrasting with a faint, but retinoid-induced, mRNA expression in promyelocytic NB4 cells," *Leukemia*, 12 (11): 1733-1740 (1998).
Tong et al., "Genomic organization of the JEM-1 (BLZF1) gene on human chromosome 1q24: molecular cloning and analysis of its promoter region," *Genomics*, 69 (3): 380-390 (Nov. 2000).
U.S. Deparment of Health and Human Services, "Minutes of the Recombinant DNA Advisory Committee," Public Health Service, National Institutes of Health, 0-A-III-1 (Dec. 4-5, 2013).
Van Beusechem et al., "Efficient and selective gene transfer into primary human brain tumors by using single-chain antibody-targeted adenoviral vectors with native tropism abolished," *J. Virol.*, 76 (6): 2753-2762 (Mar. 2002).
Verma et al., "Gene therapy-promises, problems, and prospects," *Nature*, 389: 239-242 (Sep. 18, 1997).
Wagner et al., "Nucleotide sequence of the thymidine kinase gene of herpes simplex virus type I," *Proc. Natl. Acad. Sci. USA*, 78:144-145 (1981).
Wang et al., "Second generation adenovirus vectors," *Nature Med.*, 2 (6): 714-716 (1996).
Wigand et al., "New human adenovirus (candidate adenovirus 36), a novel member of subgroup D," *Arch Virol.*, 64 (3): 225-233 (1980).
Williams et al., "Structure/function analysis on interleukin-2-toxin ($DAB_{486}$-IL-2)," *J. Biol. Chem.*, 265(20): 11885-11887 (Jul. 15, 1990).
Woo et al., "Therapeutic potential of adenovirus-mediated delivery of β-defensin 2 for experimental otitis media," *Innate Immun.*, 21(2):215-24 (Feb. 2015).
Written Opinion of the International Searching Authority, Application No. PCT/US2015/054836, dated Dec. 18, 2015.
Zajic et al., "Monoclonal antibodies to inner ear antigens: I. Antigens expressed by supporting cells of the guinea pig cochlea," *Hearing Research*, 52 (1): 59-71 (1991).
Zheng et al., "Overexpression of Math1 induces robust production of extra hair cells in postnatal rat inner ears," *Nature Neurosci.*, 3 (6): 580-586 (Jun. 2000).
Zine et al., "Hes1 and Hes5 activities are required for the normal development of the hair cells in the mammalian inner ear," *J. Neurosci.*, 21 (13): 4712-4720 (Jul. 1, 2001).
Zine, "Molecular mechanisms that regulate auditory hair-cell differentiation in the mammalian cochlea," *Mol. Neurobiol.*, 27 (2): 223-237 (Apr. 2003).
Zuo, "Transgenic and gene targeting studies of hair cell function in mouse inner ear," *J. Neurobiol.*, 53 (2): 286-305 (Nov. 2002).
Yang et al., "Regeneration of Stereocilia of Hair Cells by Forced Atoh1 Expression in the Adult Mammalian Cochlea," *PLOS One*, 7(9): 1-8 (Sep. 2012).
U.S. Appl. No. 10/373,249, filed Feb. 24, 2003.
U.S. Appl. No. 10/586,072, filed Jul. 14, 2006.
U.S. Appl. No. 13/533,322, filed Jun. 26, 2012.
U.S. Appl. No. 14/024,749, filed Sep. 12, 2013.
U.S. Appl. No. 09/585,645, filed Jun. 1, 2000.
U.S. Appl. No. 09/980,381, filed Jun. 1, 2000.
U.S. Appl. No. 10/004,717, filed Dec. 5, 2001.
U.S. Appl. No. 10/860,373, filed Jun. 3, 2004.
U.S. Appl. No. 10/860,724, filed Jun. 3, 2004.
Zhang et al., "SEM observation of hair cell progenitors forced to express Hath1 from rat cochleae," *Chin Arch Otolaryngol Head Neck Surg*, 13(5): 309-312 (2006).

```
                              SEQUENCE LISTING

<160> NUMBER OF SEQ ID NOS: 3

<210> SEQ ID NO 1
<211> LENGTH: 1065
<212> TYPE: DNA
<213> ORGANISM: Homo sapiens

<400> SEQUENCE: 1
atgtcccgcc tgctgcatgc agaagagtgg gctgaagtga aggagttggg agaccaccat      60
cgccagcccc agccgcatca tctcccgcaa ccgccgccgc cgccgcagcc acctgcaact     120
ttgcaggcga gagagcatcc cgtctacccg cctgagctgt ccctcctgga cagcaccgac     180
ccacgcgcct ggctggctcc cactttgcag ggcatctgca cggcacgcgc cgcccagtat     240
ttgctacatt ccccggagct gggtgcctca gaggccgctg cgcccgggga cgaggtggac     300 ggccggggggg agctggtaag gaggagcagc ggcggtgcca gcagcagcaa gagccccggg    360
ccggtgaaag tgcgggaaca gctgtgcaag ctgaaaggcg gggtggtggt agacgagctg     420
ggctgcagcc gccaacgggc cccttccagc aaacaggtga atggggtgca gaagcagaga     480
cggctagcag ccaacgccag ggagcggcgc aggatgcatg gctgaaccac gccttcgac     540 cagctgcgca atgttatccc gtcgttcaac aacgacaaga agctgtccaa atatgagacc     600
ctgcagatgc cccaaatcta catcaacgcc ttgtccgagc tgctacaaac gcccagcgga     660
ggggaacagc caccgccgcc tccagcctcc tgcaaaagcg accaccacca ccttcgcacc     720
gcggcctcct atgaaggggg cgcgggcaac gcgaccgcag ctggggctca gcaggcttcc     780
ggagggagcc agcggccgac cccgcccggg agttgccgga ctcgcttctc agccccagct     840
tctgcgggag ggtactcggt gcagctggac gctctgcact tctcgacttt cgaggacagc     900
gccctgacag cgatgatggc gcaaaagaat ttgtctcctt ctctccccgg gagcatcttg     960
cagccagtgc aggaggaaaa cagcaaaact tcgcctcggt cccacagaag cgacggggaa    1020 ttttccccccc attcccatta cagtgactcg gatgaggcaa gttag                   1065

<210> SEQ ID NO 2
<211> LENGTH: 2209
<212> TYPE: DNA
<213> ORGANISM: Homo sapiens

<400> SEQUENCE: 2
gagctcccac ctccctctct gtgctgggac tcacagaggg agacctcagg aggcagtctg      60
tccatcacat gtccaaatgc agagcatacc ctgggctggg cgcagtggcg cacaactgta     120
attccagcac tttgggaggc tgatgtggaa ggatcacttg agcccagaag ttctagacca     180
gcctgggcaa catggcaaga ccctatctct acaaaaaaag ttaaaaaatc agccacgtgt     240
ggtgacacac acctgtagtc ccagctattc aggaggctga ggtgagggga tcacttaagg     300
ctgggaggtt gaggctgcag tgagtcgtgg ttgcgccact gcactccagc ctgggcaaca     360
gtgagaccct gtctcaaaag acaaaaaaaa aaaaaaaaaa aaaagaaca tatcctggtg      420 tggagtaggg gacgctgctc tgacagaggc tcgggggcct gagctggctc tgtgagctgg     480
ggaggaggca gacagccagg ccttgtctgc aagcagacct ggcagcattg ggctggccgc     540
cccccagggc ctcctcttca tgcccagtga atgactcacc ttggcacaga cacaatgttc     600
```

| | |
|---|---|
| ggggtgggca cagtgcctgc ttcccgccgc acccagccc ccctcaaatg ccttccgaga | 660 |
| agcccattga gcaggggct tgcattgcac cccagcctga cagcctggca tcttgggata | 720 |
| aaagcagcac agcccctag gggctgccct tgctgtgtgg cgccaccggc ggtggagaac | 780 |
| aaggctctat tcagcctgtg cccaggaaag gggatcaggg gatgcccagg catgacagt | 840 |
| gggtggcagg gggggagagg agggctgtct gcttcccaga agtccaagga cacaaatggg | 900 |
| tgaggggact gggcagggtt ctgaccctgt gggaccagag tggagggcgt agatggacct | 960 |
| gaagtctcca gggacaacag ggcccaggtc tcaggctcct agttgggccc agtggctcca | 1020 |
| gcgtttccaa acccatccat ccccagaggt tcttcccatc tctccaggct gatgtgtggg | 1080 |
| aactcgagga aataaatctc cagtgggaga cggaggggtg gccagggaaa cggggcgctg | 1140 |
| caggaataaa gacgagccag cacagccagc tcatgtgtaa cggctttgtg gagctgtcaa | 1200 |
| ggcctggtct ctgggagaga ggcacaggga ggccagacaa gaaggggtg acctggaggg | 1260 |
| acagatccag gggctaaagt cctgataagg caagagagtg ccggcccct cttgccctat | 1320 |
| caggacctcc actgccacat agaggccatg attgacccttt agacaaaggg ctggtgtcca | 1380 |
| atcccagccc ccagccccag aactccaggg aatgaatggg cagagagcag gaatgtggga | 1440 |
| catctgtgtt caagggaagg actccaggag tctgctggga atgaggccta gtaggaaatg | 1500 |
| aggtggccct tgagggtaca gaacaggttc attcttcgcc aaattcccag caccttgcag | 1560 |
| gcacttacag ctgagtgaga taatgcctgg gttatgaaat caaaagttg gaaagcaggt | 1620 |
| cagaggtcat ctggtacagc ccttccttcc cttttttttt tttttttttg tgagacaagg | 1680 |
| tctctctctg ttgcccaggc tggagtggcg caaacacagc tcactgcagc ctcaacctac | 1740 |
| tgggctcaag caatcctcca gcctcagcct cccaaagtgc tgggattaca agcatgagcc | 1800 |
| accccactca gccctttcct tcctttttaa ttgatgcata ataattgtaa gtattcatca | 1860 |
| tggtccaacc aacccttttct tgacccacct tcctagagag agggtcctct tgcttcagcg | 1920 |
| gtcagggccc cagacccatg gtctggctcc aggtaccacc tgcctcatgc aggagttggc | 1980 |
| gtgcccagga agctctgcct ctgggcacag tgacctcagt ggggtgaggg gagctctccc | 2040 |
| catagctggg ctgcggccca accccacccc ctcaggctat gccaggggt gttgccaggg | 2100 |
| gcacccgggc atcgccagtc tagcccactc cttcataaag ccctcgcatc ccaggagcga | 2160 |
| gcagagccag agcaggttgg agaggagacg catcacctcc gctgctcgc | 2209 |

<210> SEQ ID NO 3
<211> LENGTH: 34168
<212> TYPE: DNA
<213> ORGANISM: Artificial Sequence
<220> FEATURE:
<223> OTHER INFORMATION: Synthetic

<400> SEQUENCE: 3

| | |
|---|---|
| catcatcaat aatataccttt attttggatt gaagccaata tgataatgag ggggtggagt | 60 |
| tgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgtttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggcccggga | 360 |
| tcggtgatca ccgatccaga catgataaga tacattgatg agtttggaca aaccacaact | 420 |
| agaatgcagt gaaaaaaatg ctttatttgt gaaatttgtg atgctattgc tttatttgta | 480 |

```
accattataa gctgcaataa acaagttccc ggatctttct agctagtcta gactagctag    540
actcgagagc ggccgcaatc gataagcttc taacttgcct catccgagtc actgtaatgg    600
gaatgggggg aaaattcccc gtcgcttctg tgggaccgag gcgaagtttt gctgttttcc    660
tcctgcactg gctgcaagat gctcccgggg agagaaggag acaaattctt ttgcgccatc    720
atcgctgtca gggcgctgtc ctcgaaagtc gagaagtgca gagcgtccag ctgcaccgag    780
taccctcccg cagaagctgg ggctgagaag cgagtccggc aactcccggg cggggtcggc    840
cgctggctcc ctccggaagc ctgctgagcc ccagctgcgg tcgcgttgcc cgcgccccct    900
tcataggagg ccgcggtgcg aaggtggtgg tggtcgcttt tgcaggaggc tggaggcggc    960
ggtggctgtt ccctccgct gggcgtttgt agcagctcgg acaaggcgtt gatgtagatt    1020
tgggccatct gcagggtctc atatttggac agcttcttgt cgttgttgaa cgacgggata    1080
acattgcgca gctggtcgaa ggcgtggttc agcccatgca tcctgcgccg ctccctggcg    1140
ttggctgcta gccgtctctg cttctgcacc ccattcacct gtttgctgga aggggcccgt    1200
tggcggctgc agcccagctc gtctaccacc accccgcctt tcagcttgca cagctgttcc    1260
cgcactttca ccggcccggg gctcttgctg ctgctggcac cgccgctgct cctccttacc    1320
agctccccc ggccgtccac ctcgtcccgg ggcgcagcgg cctctgaggc acccagctcc    1380
ggggaatgta gcaaatactg gcggcgcgt gccgtgcaga tgccctgcaa agtgggagcc    1440
agccaggcgc gtgggtcggt gctgtccagg agggacagct caggcgggta gacgggatgc    1500
tctctcgcct gcaaagttgc aggtggctgc ggcggcggcg gcggttgcgg gagatgatgc    1560
ggctggggct ggcgatggtg gtctcccaac tccttcactt cagcccactc ttctgcatgc    1620
agcaggcggg acatggtgga agcttgattc gactctagag gatccccgcg agcagcggag    1680
gtgatgcgtc tcctctccaa cctgctctgg ctctgctcgc tcctgggatg cgagggcttt    1740
atgaaggagt gggctagact ggcgatgccc gggtgcccct ggcaacaccc cctggcatag    1800
cctgaggggg tggggttggg ccgcagccca gctatgggga gagctcccct cacccactg    1860
aggtcactgt gcccagaggc agagcttcct gggcacgcca actcctgcat gaggcaggtg    1920
gtacctggag ccagaccatg ggtctggggc cctgaccgct gaagcaagag gaccctctct    1980
ctaggaaggt gggtcaagaa agggttggtt ggaccatgat gaatacttac aattattatg    2040
catcaattaa aaaggaagga aagggctgag tggggtggct catgcttgta atcccagcac    2100
tttgggaggc tgaggctgga ggattgcttg agcccagtag gttgaggctg cagtgagctg    2160
tgtttgcgcc actccagcct gggcaacaga gagagacctt gtctcacaaa aaaaaaaaa    2220
aaaaagggaa ggaagggctg taccagatga cctctgacct gctttccaac tttttgattt    2280
cataacccag gcattatctc actcagctgt aagtgcctgc aagtgctgg gaatttggcg    2340
aagaatgaac ctgttctgta ccctcaaggg ccacctcatt tcctactagg cctcattccc    2400
agcagactcc tggagtcctt cccttgaaca cagatgtccc acattcctgc tctctgccca    2460
ttcattccct ggagttctgg ggctggggc tgggattgga caccagccct tgtctaagg    2520
gtcaatcatg gcctctatgt ggcagtggag gtcctgatag ggcaagaggg ggccggcact    2580
ctcttgcctt atcaggactt tagccctgg atctgtccct ccaggtcacc ccttccttgt    2640
ctggcctccc tgtgcctctc tcccagagac caggccttga cagctccaca aagccgttac    2700
acatgagctg gctgtgctgg ctcgtctttta ttcctgcagc gccccgtttc cctgccacc    2760
cctccgtctc ccactggaga tttatttcct cgagttccca cacatcagcc tggagagatg    2820
```

```
ggaagaacct ctggggatgg atgggtttgg aaacgctgga gccactgggc ccaactagga    2880
gcctgagacc tgggccctgt tgtccctgga gacttcaggt ccatctacgc cctccactct    2940
ggtcccacag ggtcagaacc ctgcccagtc ccctcaccca tttgtgtcct tggacttctg    3000
ggaagcagag agccctcctc tccccccctg ccacccactg tccatgcctg ggcatcccct    3060
gatccccttt cctgggcaca ggctgaatag agccttgttc tccaccgccg gtggcgccac    3120
acagcaaggg cagcccctag ggggctgtgc tgcttttatc ccaagatgcc aggctgtcag    3180
gctggggtgc aatgcaagcc ccctgctcaa tgggcttctc ggaaggcatt tgagggggc    3240
tggggtgcgg cgggaagcag gcactgtgcc cacccgaac attgtgtctg tgccaaggtg    3300
agtcattcac tgggcatgaa gaggaggccc tggggggcgg ccagcccaat gctgccaggt    3360
ctgcttgcag acaaggcctg gctgtctgcc tcctccccag ctcacagagc cagctcaggc    3420
ccccgagcct ctgtcagagc agcgtcccct actccacacc aggatatgtt ctttttttt    3480
tttttttttt ttttgtcttt tgagacaggg tctcactgtt gcccaggctg gagtgcagtg    3540
gcgcaaccac gactcactgc agcctcaacc tcccagcctt aagtgatccc ctcacctcag    3600
cctcctgaat agctgggact acaggtgtgt gtcaccacac gtggctgatt ttttaacttt    3660
ttttgtagag atagggtctt gccatgttgc ccaggctggt ctagaacttc tgggctcaag    3720
tgatccttcc acatcagcct cccaaagtgc tggaattaca gttgtgcgcc actgcgccca    3780
gcccagggta tgctctgcat ttggacatgt gatggacaga ctgcctcctg aggtctccct    3840
ctgtgagtcc cagcacagag agggaggtgg gagctcagat ctggtaccga gctcgaattc    3900
tagtactgaa atgtgtgggc gtggcttaag ggtgggaaag aatatataag gtggggtct    3960
tatgtagttt tgtatctgtt ttgcagcagc cgccgccgcc atgagcacca actcgtttga    4020
tggaagcatt gtgagctcat atttgacaac gcgcatgccc ccatgggccg gggtgcgtca    4080
gaatgtgatg ggctccagca ttgatggtcg ccccgtcctg cccgcaaact ctactacctt    4140
gacctacgag accgtgtctg gaacgccgtt ggagactgca gcctccgccg ccgcttcagc    4200
cgctgcagcc accgcccgcg ggattgtgac tgactttgct ttcctgagcc cgcttgcaag    4260
cagtgcagct tcccgttcat ccgcccgcga tgacaagttg acggctcttt tggcacaatt    4320
ggattctttg acccgggaac ttaatgtcgt ttctcagcag ctgttggatc tgcgccagca    4380
ggtttctgcc ctgaaggctt cctcccctcc caatgcggtt taaaacataa ataaaaaacc    4440
agactctgtt tggatttgga tcaagcaagt gtcttgctgt ctttatttag gggttttgcg    4500
cgcgcggtag gccgggacc agcggtctcg gtcgttgagg gtcctgtgta ttttttccag    4560
gacgtggtaa aggtgactct ggatgttcag atacatgggc ataagcccgt ctctggggtg    4620
gaggtagcac cactgcagag cttcatgctg cggggtggtg ttgtagatga tccagtcgta    4680
gcaggagcgc tgggcgtggt gcctaaaaat gtctttcagt agcaagctga ttgccagggg    4740
caggcccttg gtgtaagtgt ttacaaagcg gttaagctgg gatgggtgca tacgtgggga    4800
tatgagatgc atcttggact gtattttag gttggctatg ttcccagcca tatccctccg    4860
gggattcatg ttgtgcagaa ccaccagcac agtgtatccg gtgcacttgg gaaatttgtc    4920
atgtagctta gaaggaaatg cgtggaagaa cttgagacg cccttgtgac ctccaagatt    4980
ttccatgcat tcgtccataa tgatggcaat gggcccacgg gcggcggcct gggcgaagat    5040
atttctggga tcactaacgt catagttgtg ttccaggatg agatcgtcat aggccatttt    5100
tacaaagcgc gggcggaggg tgccagactg cggtataatg gttccatccg gcccaggggc    5160
gtagttaccc tcacagattt gcatttccca cgctttgagt tcagatgggg ggatcatgtc    5220
```

```
tacctgcggg gcgatgaaga aaacggtttc cggggtaggg gagatcagct gggaagaaag    5280
caggttcctg agcagctgcg acttaccgca gccggtgggc ccgtaaatca cacctattac    5340
cggctgcaac tggtagttaa gagagctgca gctgccgtca tccctgagca gggggggccac   5400
ttcgttaagc atgtccctga ctcgcatgtt ttccctgacc aaatccgcca gaaggcgctc    5460
gccgcccagc gatagcagtt cttgcaagga agcaaagttt ttcaacggtt tgagaccgtc    5520
cgccgtaggc atgcttttga gcgtttgacc aagcagttcc aggcggtccc acagctcggt    5580
cacctgctct acggcatctc gatccagcat atctcctcgt ttcgcgggtt ggggcggctt    5640
tcgctgtacg gcagtagtcg gtgctcgtcc agacgggcca gggtcatgtc tttccacggg    5700
cgcagggtcc tcgtcagcgt agtctgggtc acggtgaagg ggtgcgctcc gggctgcgcg    5760
ctggccaggt gcgcttgag gctggtcctg ctggtgctga agcgctgccg gtcttcgccc     5820
tgcgcgtcgg ccaggtagca tttgaccatg gtgtcatagt ccagcccctc cgcggcgtgg    5880
cccttggcgc gcagcttgcc cttggaggag gcgccgcacg aggggcagtg cagactttg     5940
agggcgtaga gcttgggcgc gagaaatacc gattccgggg agtaggcatc cgcgccgcag    6000
gccccgcaga cggtctcgca ttccacgagc caggtgagct ctggccgttc ggggtcaaaa    6060
accaggtttc ccccatgctt tttgatgcgt ttcttacctc tggtttccat gagccggtgt    6120
ccacgctcgt tgacgaaaag gctgtccgtg tccccgtata cagacttgag aggcctgtcc    6180
tcgagcggtg ttccgcggtc ctcctcgtat agaaactcgg accactctga gacaaaggct    6240
cgcgtccagg ccagcacgaa ggaggctaag tgggaggggt agcggtcgtt gtccactagg    6300
gggtccactc gctccagggt gtgaagacac atgtcgccct cttcggcatc aaggaaggtg    6360
attggtttgt aggtgtaggc cacgtgaccg ggtgttcctg aagggggct ataaaagggg     6420
gtggggcgc gttcgtcctc actctcttcc gcatcgctgt ctgcgagggc cagctgttgg     6480
ggtgagtact ccctctgaaa agcgggcatg acttctgcgc taagattgtc agtttccaaa    6540
aacgaggagg atttgatatt cacctggccc gcggtgatgc ctttgagggt ggccgcatcc    6600
atctggtcag aaaagacaat cttttttgttg tcaagcttgg tggcaaacga cccgtagagg    6660
gcgttggaca gcaacttggc gatggagcgc agggtttggt ttttgtcgcg atcggcgcgc    6720
tccttggccg cgatgtttag ctgcacgtat tcgcgcgcaa cgcaccgcca ttcgggaaag    6780
acggtggtgc gctcgtcggg caccaggtgc acgcgccaac cgcggttgtg cagggtgaca    6840
aggtcaacgc tggtggctac ctctccgcgt aggcgctcgt tggtccagca gaggcggccg    6900
cccttgcgcg agcagaatgg cggtaggggg tctagctgcg tctcgtccgg ggggtctgcg    6960
tccacggtaa agaccccggg cagcaggcgc gcgtcgaagt agtctatctt gcatccttgc    7020
aagtctagcg cctgctgcca tgcgcgggcg gcaagcgcgc gctcgtatgg gttgagtggg    7080
ggaccccatg gcatggggtg ggtgagcgcg gaggcgtaca tgccgcaaat gtcgtaaacg    7140
tagagggct ctctgagtat tccaagatat gtagggtagc atcttccacc gcggatgctg     7200
gcgcgcacgt aatcgtatag ttcgtgcgag ggagcgagga ggtcgggacc gaggttgcta    7260
cgggcgggct gctctgctcg gaagactatc tgcctgaaga tggcatgtga gttggatgat    7320
atggttggac gctggaagac gttgaagctg gcgtctgtga gacctaccgc gtcacgcacg    7380
aaggaggcgt aggagtcgcg cagcttgttg accagctcgg cggtgacctg cacgtctagg    7440
gcgcagtagt ccagggtttc cttgatgatg tcatacttat cctgtccctt ttttttccac    7500
agctcgcggt tgaggacaaa ctcttcgcgg tctttccagt actcttggat cggaaacccg    7560
```

```
tcggcctccg aacggtaaga gcctagcatg tagaactggt tgacggcctg gtaggcgcag    7620
catccctttt ctacgggtag cgcgtatgcc tgcgcggcct tccggagcga ggtgtgggtg    7680
agcgcaaagg tgtccctgac catgactttg aggtactggt atttgaagtc agtgtcgtcg    7740
catccgccct gctcccagag caaaaagtcc gtgcgctttt tggaacgcgg atttggcagg    7800
gcgaaggtga catcgttgaa gagtatcttt cccgcgcgag gcataaagtt gcgtgtgatg    7860
cggaagggtc ccggcacctc ggaacggttg ttaattacct gggcggcgag cacgatctcg    7920
tcaaagccgt tgatgttgtg cccacaatg taaagttcca agaagcgcgg gatgcccttg     7980
atggaaggca attttttaag ttcctcgtag gtgagctctt caggggagct gagcccgtgc    8040
tctgaaaggg cccagtctgc aagatgaggg ttggaagcga cgaatgagct ccacaggtca    8100
cgggccatta gcatttgcag gtggtcgcga aaggtcctaa actggcgacc tatggccatt    8160
ttttctgggg tgatgcagta aaggtaagc gggtcttgtt cccagcggtc ccatccaagg     8220
ttcgcggcta ggtctcgcgc ggcagtcact agaggctcat ctccgccgaa cttcatgacc    8280
agcatgaagg gcacgagctg cttcccaaag gcccccatcc aagtataggt ctctacatcg    8340
taggtgacaa agagacgctc ggtgcgagga tgcgagccga tcgggaagaa ctggatctcc    8400
cgccaccaat tggaggagtg gctattgatg tggtgaaagt agaagtccct gcgacgggcc    8460
gaacactcgt gctggctttt gtaaaaacgt gcgcagtact ggcagcggtg cacgggctgt    8520
acatcctgca cgaggttgac ctgacgaccg cgcacaagga agcagagtgg gaatttgagc    8580
ccctcgcctg gcgggtttgg ctggtggtct tctacttcgg ctgcttgtcc ttgaccgtct    8640
ggctgctcga ggggagttac ggtggatcgg accaccacgc cgcgcgagcc caaagtccag    8700
atgtccgcgc gcggcggtcg gagcttgatg acaacatcgc gcagatggga gctgtccatg    8760
gtctggagct cccgcggcgt caggtcaggc gggagctcct gcaggtttac ctcgcataga    8820
cgggtcaggg cgcgggctag atccaggtga tacctaattt ccaggggctg gttggtggcg    8880
gcgtcgatgg cttgcaagag gccgcatccc cgcggcgcga ctacggtacc gcgcggcggg    8940
cggtgggccg cggggagtgtc cttggatgat gcatctaaaa gcggtgacgc gggcgagccc    9000
ccggaggtag ggggggctcc ggacccgccg ggagagggg caggggcacg tcggcgccgc     9060
gcgcgggcag gagctggtgc tgcgcgcgta ggttgctggc gaacgcgacg acgcggcggt    9120
tgatctcctg aatctggcgc ctctgcgtga agacgacggg cccggtgagc ttgaacctga    9180
aagagagttc gacagaatca atttcggtgt cgttgacggc ggcctggcgc aaaatctcct    9240
gcacgtctcc tgagttgtct tgataggcga tctcggccat gaactgctcg atctcttcct    9300
cctggagatc tccgcgtccg gctcgctcca cggtggcggc gaggtcgttg gaaatgcggg    9360
ccatgagctg cgagaaggcg ttgaggcctc cctcgttcca gacgcggctg tagaccacgc    9420
ccccttcggc atcgcgggcg cgcatgacca cctgcgcgag attgagctcc acgtgccggg    9480
cgaagacggc gtagtttcgc aggcgctgaa agaggtagtt gagggtggtg gcggtgtgtt    9540
ctgccacgaa gaagtacata acccagcgtc gcaacgtgga ttcgttgata tcccccaagg    9600
cctcaaggcg ctccatggcc tcgtagaagt ccacggcgaa gttgaaaaac tgggagttgc    9660
gcgccgacac ggttaactcc tcctccagaa gacggatgag ctcggcgaca gtgtcgcgca    9720
cctcgcgctc aaaggctaca ggggcctctt cttcttcttc aatctcctct tccataaggg    9780
cctccccttc ttcttcttct ggcggcggtg ggggaggggg gacacggcgg cgacgacggg    9840
gcaccggagg gcggtcgaca aagcgctcga tcatctcccc gcggcgacgg cgcatggtct    9900
cggtgacggc gcggccgttc tcgcggggc gcagttggaa gacgccgccc gtcatgtccc     9960
```

```
ggttatgggt tggcgggggg ctgccatgcg gcagggatac ggcgctaacg atgcatctca    10020
acaattgttg tgtaggtact ccgccgccga gggacctgag cgagtccgca tcgaccggat    10080
cggaaaacct ctcgagaaag gcgtctaacc agtcacagtc gcaaggtagg ctgagcaccg    10140
tggcgggcgg cagcgggcgg cggtcggggt tgtttctggc ggaggtgctg ctgatgatgt    10200
aattaaagta ggcggtcttg agacggcgga tggtcgacag aagcaccatg tccttgggtc    10260
cggcctgctg aatgcgcagg cggtcggcca tgccccaggc ttcgttttga catcggcgca    10320
ggtctttgta gtagtcttgc atgagccttt ctaccggcac ttcttcttct ccttcctctt    10380
gtcctgcatc tcttgcatct atcgctgcgg cggcggcgga gtttggccgt aggtggcgcc    10440
ctcttcctcc catgcgtgtg accccgaagc ccctcatcgg ctgaagcagg gctaggtcgg    10500
cgacaacgcg ctcggctaat atggcctgct gcacctgcgt gagggtagac tggaagtcat    10560
ccatgtccac aaagcggtgg tatgcgcccg tgttgatggt gtaagtgcag ttggccataa    10620
cggaccagtt aacggtctgg tgacccggct gcgagagctc ggtgtacctg agacgcgagt    10680
aagccctcga gtcaaatacg tagtcgttgc aagtccgcac caggtactgg tatcccacca    10740
aaaagtgcgg cggcggctgg cggtagaggg gccagcgtag ggtggccggg gctccggggg    10800
cgagatcttc aacataagg cgatgatatc cgtagatgta cctggacatc caggtgatgc    10860
cggcggcggt ggtggaggcg cgcggaaagt cgcggacgcg gttccagatg ttgcgcagcg    10920
gcaaaaagtg ctccatggtc gggacgctct ggccggtcag gcgcgcgcaa tcgttgacgc    10980
tctagcgtgc aaaaggagag cctgtaagcg ggcactcttc cgtggtctgg tggataaatt    11040
cgcaagggta tcatggcgga cgaccggggt tcgagccccg tatccggccg tccgccgtga    11100
tccatgcggt taccgcccgc gtgtcgaacc caggtgtgcg acgtcagaca acggggagt    11160 gctccttttg gcttccttcc aggcgcggcg gctgctgcgc tagcttttt ggccactggc    11220 cgcgcgcagc gtaagcggtt aggctggaaa gcgaaagcat taagtggctc gctccctgta    11280
gccggagggt tattttccaa gggttgagtc gcgggacccc cggttcgagt ctcggaccgg    11340
ccggactgcg gcgaacgggg gtttgcctcc ccgtcatgca agaccccgct tgcaaattcc    11400
tccggaaaca gggacgagcc cctttttgc ttttcccaga tgcatccggt gctgcggcag    11460
atgcgccccc ctcctcagca gcggcaagag caagagcagc ggcagacatg cagggcaccc    11520
tcccctcctc ctaccgcgtc aggaggggcg acatccgcgg ttgacgcggc agcagatggt    11580
gattacgaac ccccgcggcg ccgggcccgg cactacctgg acttggagga gggcgagggc    11640
ctggcgcggc taggagcgcc ctctcctgag cggcacccaa gggtgcagct gaagcgtgat    11700
acgcgtgagg cgtacgtgcc gcggcagaac ctgtttcgcg accgcgaggg agaggagccc    11760
gaggagatgc gggatcgaaa gttccacgca gggcgcgagc tgcggcatgg cctgaatcgc    11820
gagcggttgc tgcgcgagga ggactttgag cccgacgcgc gaaccgggat tagtcccgcg    11880
cgcgcacacg tggcggccgc cgacctggta accgcatacg agcagacggt gaaccaggag    11940
attaactttc aaaaaagctt taacaaccac gtgcgtacgc ttgtggcgcg cgaggaggtg    12000
gctataggac tgatgcatct gtgggacttt gtaagcgcgc tggagcaaaa cccaaatagc    12060
aagccgctca tggcgcagct gttccttata gtgcagcaca gcagggacaa cgaggcattc    12120
agggatgcgc tgctaaacat agtagagccc gagggccgct ggctgctcga tttgataaac    12180
atcctgcaga gcatagtggt gcaggagcgc agcttgagcc tggctgacaa ggtggccgcc    12240
atcaactatt ccatgcttag cctgggcaag ttttacgccc gcaagatata ccatacccct    12300
```

```
tacgttccca tagacaagga ggtaaagatc gaggggttct acatgcgcat ggcgctgaag    12360
gtgcttacct tgagcgacga cctgggcgtt tatcgcaacg agcgcatcca caaggccgtg    12420
agcgtgagcc ggcggcgcga gctcagcgac cgcgagctga tgcacagcct gcaaagggcc    12480
ctggctggca cgggcagcgg cgatagagag gccgagtcct actttgacgc gggcgctgac    12540
ctgcgctggg ccccaagccg acgcgccctg gaggcagctg gggccggacc tgggctggcg    12600
gtggcacccg cgcgcgctgg caacgtcggc ggcgtggagg aatatgacga ggacgatgag    12660
tacgagccag aggacggcga gtactaagcg gtgatgtttc tgatcagatg atgcaagacg    12720
caacggaccc ggcggtgcgg gcggcgctgc agagccagcc gtccggcctt aactccacgg    12780
acgactggcg ccaggtcatg gaccgcatca tgtcgctgac tgcgcgcaat cctgacgcgt    12840
tccggcagca gccgcaggcc aaccggctct ccgcaattct ggaagcggtg gtcccggcgc    12900
gcgcaaaccc cacgcacgag aaggtgctgg cgatcgtaaa cgcgctggcc gaaaacaggg    12960
ccatccggcc cgacgaggcc ggcctggtct acgacgcgct gcttcagcgc gtggctcgtt    13020
acaacagcgg caacgtgcag accaacctgg accggctggt gggggatgtg cgcgaggccg    13080
tggcgcagcg tgagcgcgcg cagcagcagg gcaacctggg ctccatggtt gcactaaacg    13140
ccttcctgag tacacagccc gccaacgtgc cgcggggaca ggaggactac accaactttg    13200
tgagcgcact gcggctaatg gtgactgaga caccgcaaag tgaggtgtac cagtctgggc    13260
cagactattt tttccagacc agtagacaag gcctgcagac cgtaaacctg agccaggctt    13320
tcaaaaactt gcaggggctg tggggggtgc gggctcccac aggcgaccgc gcgaccgtgt    13380
ctagcttgct gacgcccaac tcgcgcctgt tgctgctgct aatagcgccc ttcacggaca    13440
gtggcagcgt gtcccgggac acatacctag gtcacttgct gacactgtac cgcgaggcca    13500
taggtcaggc gcatgtggac gagcatactt tccaggagat tacaagtgtc agccgcgcgc    13560
tggggcagga ggacacgggc agcctggagg caaccctaaa ctacctgctg accaaccggc    13620
ggcagaagat cccctcgttg cacagtttaa acagcgagga ggagcgcatt ttgcgctacg    13680
tgcagcagag cgtgagcctt aacctgatgc gcgacggggt aacgcccagc gtggcgctgg    13740
acatgaccgc gcgcaacatg gaaccgggca tgtatgcctc aaaccggccg tttatcaacc    13800
gcctaatgga ctacttgcat cgcgcggccg ccgtgaaccc cgagtatttc accaatgcca    13860
tcttgaaccc gcactggcta ccgccccctg gtttctacac cggggattc gaggtgcccg    13920 agggtaacga tggattcctc tgggacgaca tagacgacag cgtgttttcc ccgcaaccgc    13980 agacctgct agagttgcaa cagcgcgagc aggcagaggc ggcgctgcga aaggaaagct    14040
tccgcaggcc aagcagcttg tccgatctag gcgctgcggc cccgcggtca gatgctagta    14100 gcccattcc aagcttgata gggtctctta ccagcactcg caccaccgc ccgcgcctgc     14160 tgggcgagga ggagtaccta aacaactcgc tgctgcagcc gcagcgcgaa aaaaacctgc    14220
ctccggcatt tccaacaac gggatagaga gcctagtgga caagatgagt agatggaaga    14280
cgtacgcgca ggagcacagg gacgtgccag gcccgcgccc gccacccgt cgtcaaaggc     14340 acgaccgtca gcggggtctg gtgtgggagg acgatgactc ggcagacgac agcagcgtcc    14400
tggatttggg agggagtggc aacccgtttg cgcaccttcg ccccaggctg gggagaatgt    14460
tttaaaaaaa aaaaagcat gatgcaaaat aaaaaactca ccaaggccat ggcaccgagc     14520
gttggttttc ttgtattccc cttagtatgc ggcgcgcggc gatgtatgag gaaggtcctc    14580
ctccctccta cgagagtgtg gtgagcgcgg cgccagtggc ggcggcgctg ggttctccct    14640
tcgatgctcc cctggacccg ccgtttgtgc ctccgcggta cctgcggcct accgggggga    14700
```

```
gaaacagcat ccgttactct gagttggcac ccctattcga caccaccgt gtgtacctgg   14760 tggacaacaa gtcaacggat gtggcatccc tgaactacca gaacgaccac agcaacttc   14820 tgaccacggt cattcaaaac aatgactaca gcccggggga ggcaagcaca cagaccatca   14880
atcttgacga ccggtcgcac tggggcggcg acctgaaaac catcctgcat accaacatgc   14940
caaatgtgaa cgagttcatg tttaccaata agtttaaggc gcgggtgatg gtgtcgcgct   15000
tgcctactaa ggacaatcag gtggagctga aatacgagtg ggtggagttc acgctgcccg   15060
agggcaacta ctccgagacc atgaccatag accttatgaa caacgcgatc gtggagcact   15120
acttgaaagt gggcagacag aacggggttc tggaaagcga catcggggta aagtttgaca   15180
cccgcaactt cagactgggg tttgaccccg tcactggtct tgtcatgcct ggggtatata   15240
caaacgaagc cttccatcca gacatcattt tgctgccagg atgcggggtg gacttcaccc   15300
acagccgcct gagcaacttg ttgggcatcc gcaagcggca acccttccag gagggcttta   15360
ggatcaccta cgatgatctg gagggtggta acattcccgc actgttggat gtggacgcct   15420
accaggcgag cttgaaagat gacaccgaac agggcggggg tggcgcaggc ggcagcaaca   15480
gcagtggcag cggcgcggaa gagaactcca acgcggcagc cgcggcaatg cagccggtgg   15540
aggacatgaa cgatcatgcc attcgcggcg acaccttgc cacacgggct gaggagaagc   15600
gcgctgaggc cgaagcagcg gccgaagctg ccgcccccgc tgcgcaaccc gaggtcgaga   15660
agcctcagaa gaaaccggtg atcaaacccc tgacagagga cagcaagaaa cgcagttaca   15720
acctaataag caatgacagc accttcaccc agtaccgcag ctggtacctt gcatacaact   15780
acggcgaccc tcagaccgga atccgctcat ggaccctgct ttgcactcct gacgtaaacct   15840 gcggctcgga gcaggtctac tggtcgttgc cagacatgat gcaagacccc gtgaccttcc   15900
gctccacgcg ccagatcagc aacttttccgg tggtgggcgc cgagctgttg cccgtgcact   15960
ccaagagctt ctacaacgac caggccgtct actcccaact catccgccag tttacctctc   16020
tgacccacgt gttcaatcgc tttcccgaga accagatttt ggcgcgcccg ccagccccca   16080
ccatcaccac cgtcagtgaa aacgttcctg ctctcacaga tcacgggacg ctaccgctgc   16140
gcaacagcat cggaggagtc cagcgagtga ccattactga cgccagacgc cgcacctgcc   16200
cctacgttta caaggccctg ggcatagtct cgccgcgcgt cctatcgagc cgcactttt   16260 gagcaagcat gtccatcctt atatcgccca gcaataacac aggctgggc ctgcgcttcc   16320 caagcaagat gtttggcggg gccaagaagc gctccgacca acacccagtg cgcgtgcgcg   16380
ggcactaccg cgcgccctgg ggcgcgcaca aacgcggccg cactgggcgc accaccgtcg   16440
atgacgccat cgacgcggtg gtggaggagg cgcgcaacta cacgcccacg ccgccaccag   16500
tgtccacagt ggacgcggcc attcagaccg tggtgcgcgg agcccggcgc tatgctaaaa   16560
tgaagagacg gcggaggcgc gtagcacgtc gccaccgccg ccgacccggc actgccgccc   16620
aacgcgcggc ggcggccctg cttaaccgcg cacgtcgcac cggccgacgg gcggccatgc   16680
gggccgctcg aaggctggcc gcgggtattg tcactgtgcc ccccaggtcc aggcgacgag   16740
cggccgccgc agcagccgcg gccattagtg ctatgactca gggtcgcagg ggcaacgtgt   16800
attgggtgcg cgactcggtt agcggcctgc gcgtgcccgt gcgcacccgc ccccgcgca   16860 actagattgc aagaaaaaac tacttagact cgtactgttg tatgtatcca gcggcggcgg   16920
cgcgcaacga agctatgtcc aagcgcaaaa tcaaagaaga gatgctccag gtcatcgcgc   16980
cggagatcta tggcccccg aagaaggaag agcaggatta caagcccga aagctaaagc   17040
```

```
gggtcaaaaa gaaaagaaa gatgatgatg atgaacttga cgacgaggtg gaactgctgc   17100
acgctaccgc gcccaggcga cgggtacagt ggaaaggtcg acgcgtaaaa cgtgttttgc   17160
gacccggcac caccgtagtc tttacgcccg gtgagcgctc cacccgcacc tacaagcgcg   17220
tgtatgatga ggtgtacggc gacgaggacc tgcttgagca ggccaacgag cgcctcgggg   17280
agtttgccta cggaaagcgg cataaggaca tgctggcgtt gccgctggac gagggcaacc   17340
caacacctag cctaaagccc gtaacactgc agcaggtgct gcccgcgctt gcaccgtccg   17400
aagaaaagcg cggcctaaag cgcgagtctg gtgacttggc acccaccgtg cagctgatgg   17460
tacccaagcg ccagcgactg gaagatgtct tggaaaaaat gaccgtggaa cctgggctgg   17520
agcccgaggt ccgcgtgcgg ccaatcaagc aggtggcgcc gggactgggc gtgcagaccg   17580
tggacgttca gatacccact accagtagca ccagtattgc caccgccaca gagggcatgg   17640
agacacaaac gtccccggtt gcctcagcgg tggcggatgc cgcggtgcag gcggtcgctg   17700
cggccgcgtc caagacctct acggaggtgc aaacggaccc gtggatgttt cgcgtttcag   17760 cccccggcg cccgcgccgt tcgaggaagt acggcgccgc cagcgcgcta ctgcccgaat   17820
atgccctaca tccttccatt gcgcctaccc ccggctatcg tggctacacc taccgcccca   17880
gaagacgagc aactacccga cgccgaacca ccactggaaa ccgccgccgc cgtcgccgtc   17940
gccagcccgt gctggccccg atttccgtgc gcagggtggc tcgcgaagga ggcaggaccc   18000
tggtgctgcc aacagcgcgc taccacccca gcatcgttta aaagccggtc tttgtggttc   18060
ttgcagatat ggccctcacc tgccgcctcc gtttcccggt gccgggattc cgaggaagaa   18120
tgcaccgtag gaggggcatg gccggccacg gcctgacggg cggcatgcgt cgtgcgcacc   18180
accggcggcg gcgcgcgtcg caccgtcgca tgcgcggcgg tatcctgccc ctccttattc   18240
cactgatcgc cgcggcgatt ggcgccgtgc ccggaattgc atccgtggcc ttgcaggcgc   18300
agagacactg attaaaaaca agttgcatgt ggaaaaatca aaataaaaag tctggactct   18360
cacgctcgct tggtcctgta actattttgt agaatggaag acatcaactt gcgtctctg   18420 gccccgcgac acggctcgcg cccgttcatg ggaaactggc aagatatcgg caccagcaat   18480
atgagcggtg gcgccttcag ctggggctcg ctgtggagcg gcattaaaaa tttcggttcc   18540
accgttaaga actatggcag caaggcctgg aacagcagca caggccagat gctgagggat   18600
aagttgaaag agcaaaattt ccaacaaaag gtggtagatg gcctggcctc tggcattagc   18660
ggggtggtgg acctggccaa ccaggcagtg caaaataaga ttaacagtaa gcttgatccc   18720
cgccctcccg tagaggagcc tccaccggcc gtggagacag tgtctccaga ggggcgtggc   18780
gaaaagcgtc gcgcccccga cagggaagaa actctggtga cgcaaataga cgagcctccc   18840
tcgtacgagg aggcactaaa gcaaggcctg cccaccaccc gtcccatcgc gcccatggct   18900
accggagtgc tgggccagca cacacccgta acgctggacc tgcctccccc cgccgacacc   18960
cagcagaaac ctgtgctgcc aggcccgacc gccgttgttg taacccgtcc tagccgcgcg   19020
tccctgcgcc gcgccgccag cggtccgcga tcgttgcggc ccgtagccag tggcaactgg   19080
caaagcacac tgaacagcat cgtgggtctg ggggtgcaat ccctgaagcg ccgacgatgc   19140
ttctgatagc taacgtgtcg tatgtgtgtc atgtatgcgt ccatgtcgcc gccagaggag   19200
ctgctgagcc gccgcgcgcc cgcttttcaa gatggctacc ccttcgatga tgccgcagtg   19260
gtcttacatg cacatctcgg gccaggacgc ctcggagtac ctgagcccg gctggtgca   19320 gtttgccccgc gccaccgaga cgtacttcag cctgaataac aagtttagaa accccacggt   19380
ggcgcctacg cacgacgtga ccacagaccg gtcccagcgt ttgacgctgc ggttcatccc   19440
```

```
tgtggaccgt gaggatactg cgtactcgta caaggcgcgg ttcaccctag ctgtgggtga    19500
taaccgtgtg ctggacatgg cttccacgta ctttgacatc cgcggcgtgc tggacagggg    19560
ccctactttt aagccctact ctggcactgc ctacaacgcc ctggctccca agggtgcccc    19620
aaatccttgc gaatgggatg aagctgctac tgctcttgaa ataaacctag aagaagagga    19680
cgatgacaac gaagacgaag tagacgagca agctgagcag caaaaaactc acgtatttgg    19740
gcaggcgcct tattctggta taaatattac aaaggagggt attcaaatag gtgtcgaagg    19800
tcaaacacct aaatatgccg ataaaacatt tcaacctgaa cctcaaatag gagaatctca    19860
gtggtacgaa acagaaatta atcatgcagc tgggagagtc ctaaaaaaga ctaccccaat    19920
gaaaccatgt tacggttcat atgcaaaacc cacaaatgaa aatggagggc aaggcattct    19980
tgtaaagcaa caaaatggaa agctagaaag tcaagtggaa atgcaattt tctcaactac     20040 tgaggcagcc gcaggcaatg gtgataactt gactcctaaa gtggtattgt acagtgaaga    20100
tgtagatata gaaaccccag acactcatat ttcttacatg cccactatta aggaaggtaa    20160
ctcacgagaa ctaatgggcc aacaatctat gcccaacagg cctaattaca ttgcttttag    20220
ggacaatttt attggtctaa tgtattacaa cagcacgggt aatatgggtg ttctggcggg    20280
ccaagcatcg cagttgaatg ctgttgtaga tttgcaagac agaaacacag agctttcata    20340
ccagcttttg cttgattcca ttggtgatag aaccaggtac ttttctatgt ggaatcaggc    20400
tgttgacagc tatgatccag atgttagaat tattgaaaat catggaactg aagatgaact    20460
tccaaattac tgcttttccac tgggaggtgt gattaataca gagactctta ccaaggtaaa    20520
acctaaaaca ggtcaggaaa atggatggga aaagatgct acagaatttt cagataaaaa     20580
tgaaataaga gttggaaata ttttgccat ggaaatcaat ctaaatgcca acctgtggag     20640
aaatttcctg tactccaaca tagcgctgta tttgcccgac aagctaaagt acagtccttc    20700
caacgtaaaa atttctgata acccaaacac ctacgactac atgaacaagc gagtggtggc    20760
tcccgggcta gtggactgct acattaacct tggagcacgc tggtcccttg actatatgga    20820
caacgtcaac ccatttaacc accaccgcaa tgctggcctg cgctaccgct caatgttgct    20880
gggcaatggt cgctatgtgc ccttccacat ccaggtgcct cagaagttct ttgccattaa    20940
aaacctcctt ctcctgccgg gctcatacac ctacgagtgg aacttcagga aggatgttaa    21000
catggttctg cagagctccc taggaaatga cctaagggtt gacggagcca gcattaagtt    21060
tgatagcatt tgcctttacg ccaccttctt ccccatggcc cacaacaccg cctccacgct    21120
tgaggccatg cttagaaacg acaccaacga ccagtccttt aacgactatc tctccgccgc    21180
caacatgctc taccctatac ccgccaacgc taccaacgtg cccatatcca tccctcccg    21240 caactgggcg gctttccgcg gctgggcctt cacgcgcctt aagactaagg aaacccatc    21300 actgggctcg ggctacgacc ttattacac ctactctggc tctataccct acctagatgg    21360 aacctttac ctcaaccaca cctttaagaa ggtggccatt acctttgact cttctgtcag    21420
ctggcctggc aatgaccgcc tgcttacccc caacgagttt gaaattaagc gctcagttga    21480 cgggagggt tacaacgttg cccagtgtaa catgaccaaa gactggttcc tggtacaaat    21540
gctagctaac tataacattg gctaccaggg cttctatatc ccagagagct acaaggaccg    21600
catgtactcc ttctttagaa acttccagcc catgagccgt caggtggtgg atgatactaa    21660
atacaaggac taccaacagg tgggcatcct acaccaacac aacaactctg gatttgttgg    21720
ctaccttgcc cccaccatgc gcgaaggaca ggcctaccct gctaacttcc cctatccgct    21780
```

```
tataggcaag accgcagttg acagcattac ccagaaaaag tttctttgcg atcgcaccct   21840
ttggcgcatc ccattctcca gtaactttat gtccatgggc gcactcacag acctgggcca   21900
aaaccttctc tacgccaact ccgcccacgc gctagacatg acttttgagg tggatcccat   21960
ggacgagccc acccttcttt atgttttgtt tgaagtcttt gacgtggtcc gtgtgcacca   22020
gccgcaccgc ggcgtcatcg aaaccgtgta cctgcgcacg cccttctcgg ccggcaacgc   22080
cacaacataa agaagcaagc aacatcaaca acagctgccg ccatgggctc cagtgagcag   22140
gaactgaaag ccattgtcaa agatcttggt tgtgggccat attttttggg cacctatgac   22200
aagcgctttc caggctttgt ttctccacac aagctcgcct gcgccatagt caatacggcc   22260
ggtcgcgaga ctggggggcgt acactggatg gcctttgcct ggaacccgca ctcaaaaaca   22320
tgctacctct ttgagccctt tggcttttct gaccagcgac tcaagcaggt ttaccagttt   22380
gagtacgagt cactcctgcg ccgtagcgcc attgcttctt cccccgaccg ctgtataacg   22440
ctggaaaagt ccacccaaag cgtacagggg cccaactcgg ccgcctgtgg actattctgc   22500
tgcatgtttc tccacgcctt tgccaactgg ccccaaactc ccatggatca aaccccacc   22560
atgaaccttta ttaccggggt acccaactcc atgctcaaca gtccccaggt acagcccacc   22620
ctgcgtcgca accaggaaca gctctacagc ttcctggagc gccactcgcc ctacttccgc   22680
agccacagtg cgcagattag gagcgccact tcttttttgtc acttgaaaaa catgtaaaaa   22740
taatgtacta gagacacttt caataaaggc aaatgctttt atttgtacac tctcgggtga   22800
ttatttaccc ccacccttgc cgtctgcgcc gtttaaaaat caaggggggtt ctgccgcgca   22860
tcgctatgcg ccactggcag ggacacgttg cgatactggt gtttagtgct ccacttaaac   22920
tcaggcacaa ccatccgcgg cagctcggtg aagttttcac tccacaggct gcgcaccatc   22980
accaacgcgt ttagcaggtc gggcgccgat atcttgaagt cgcagttggg gcctccgccc   23040
tgcgcgcgcg agttgcgata cacagggttg cagcactgga acactatcag cgccgggtgg   23100
tgcacgctgg ccagcacgct cttgtcggag atcagatccg cgtccaggtc ctccgcgttg   23160
ctcagggcga acggagtcaa ctttggtagc tgccttccca aaagggcgc gtgcccaggc   23220
tttgagttgc actcgcaccg tagtggcatc aaaaggtgac cgtgcccggt ctgggcgtta   23280
ggatacagcg cctgcataaa agccttgatc tgcttaaaag ccacctgagc cctttgcgcct   23340
tcagagaaga acatgccgca agacttgccg gaaaactgat tggccggaca ggccgcgtcg   23400
tgcacgcagc accttgcgtc ggtgttggag atctgcacca catttcggcc ccaccggttc   23460
ttcacgatct tggccttgct agactgctcc ttcagcgcgc gctgcccgtt ttcgctcgtc   23520
acatccatt caatcacgtg ctccttattt atcataatgc ttccgtgtag acacttaagc   23580
tcgccttcga tctcagcgca gcggtgcagc cacaacgcgc agcccgtggg ctcgtgatgc   23640
ttgtaggtca cctctgcaaa cgactgcagg tacgcctgca ggaatcgccc catcatcgtc   23700
acaaaggtct tgttgctggt gaaggtcagc tgcaacccgc ggtgctcctc gttcagccag   23760
gtcttgcata cggccgccag agcttccact tggtcaggca gtagtttgaa gttcgccttt   23820
agatcgttat ccacgtggta cttgtccatc agcgcgcgcg cagcctccat gcccttctcc   23880
cacgcagaca cgatcggcac actcagcggg ttcatcaccg taatttcact ttccgcttcg   23940
ctgggctctt cctcttcctc ttgcgtccgc ataccacgcg ccactgggtc gtcttcattc   24000
agccgccgca ctgtgcgctt acctcctttg ccatgcttga ttagcaccgg tgggttgctg   24060
aaacccacca tttgtagcgc cacatcttct ctttcttcct cgctgtccac gattacctct   24120
ggtgatggcg ggcgctcggg cttgggagaa gggcgcttct tttctcttct gggcgcaatg   24180
```

```
gccaaatccg ccgccgaggt cgatggccgc gggctgggtg tgcgcggcac cagcgcgtct   24240
tgtgatgagt cttcctcgtc ctcggactcg atacgccgcc tcatccgctt ttttgggggc   24300
gcccggggag gcggcggcga cggggacggg gacgacacgt cctccatggt tgggggacgt   24360
cgcgccgcac cgcgtccgcg ctcggggggtg gtttcgcgct gctcctcttc ccgactggcc   24420
atttccttct cctataggca gaaaagatc atggagtcag tcgagaagaa ggacagccta   24480
accgccccct ctgagttcgc caccaccgcc tccaccgatg ccgccaacgc gcctaccacc   24540
ttccccgtcg aggcaccccc gcttgaggag gaggaagtga ttatcgagca ggacccaggt   24600
tttgtaagcg aagacgacga ggaccgctca gtaccaacag aggataaaaa gcaagaccag   24660
gacaacgcag aggcaaacga ggaacaagtc gggcgggggg acgaaaggca tggcgactac   24720
ctagatgtgg gagacgacgt gctgttgaag catctgcagc gccagtgcgc cattatctgc   24780
gacgcgttgc aagagcgcag cgatgtgccc ctcgccatag cggatgtcag ccttgcctac   24840
gaacgccacc tattctcacc gcgcgtaccc cccaaacgcc aagaaaacgg cacatgcgag   24900
cccaacccgc gcctcaactt ctaccccgta tttgccgtgc cagaggtgct tgccacctat   24960
cacatctttt tccaaaactg caagataccc ctatcctgcc gtgccaaccg cagccgagcg   25020
gacaagcagc tggccttgcg gcagggcgct gtcatacctg atatcgcctc gctcaacgaa   25080
gtgccaaaaa tctttgaggg tcttggacgc gacgagaagc gcgcggcaaa cgctctgcaa   25140
caggaaaaca gcgaaaatga aagtcactct ggagtgttgg tggaactcga gggtgacaac   25200
gcgcgcctag ccgtactaaa acgcagcatc gaggtcaccc actttgccta cccggcactt   25260
aacctacccc ccaaggtcat gagcacagtc atgagtgagc tgatcgtgcg ccgtgcgcag   25320
cccctggaga gggatgcaaa tttgcaagaa caaacagagg agggcctacc cgcagttggc   25380
gacgagcagc tagcgcgctg gcttcaaacg cgcgagcctg ccgacttgga ggagcgacgc   25440
aaactaatga tggccgcagt gctcgttacc gtggagcttg agtgcatgca gcggttcttt   25500
gctgacccgg agatgcagcg caagctagag gaaacattgc actacacctt tcgacagggc   25560
tacgtacgcc aggcctgcaa gatctccaac gtggagctct gcaacctggt ctcctacctt   25620
ggaattttgc acgaaaaccg ccttgggcaa aacgtgcttc attccacgct caagggcgag   25680
gcgcgccgcg actacgtccg cgactgcgtt tacttatttc tatgctacac ctggcagacg   25740
gccatgggcg tttggcagca gtgcttggag gagtgcaacc tcaaggagct gcagaaactg   25800
ctaaagcaaa acttgaagga cctatggacg gccttcaacg agcgctccgt ggccgcgcac   25860
ctggcggaca tcattttccc cgaacgcctg cttaaaaccc tgcaacaggg tctgccagac   25920
ttcaccagtc aaagcatgtt gcagaacttt aggaacttta tcctagagcg ctcaggaatc   25980
ttgccccgca cctgctgtgc acttcctagc gactttgtgc ccattaagta ccgcgaatgc   26040
cctccgccgc tttggggcca ctgctaccct ctgcagctag ccaactacct tgcctaccac   26100
tctgacataa tggaagacgt gagcggtgac ggtctactgg agtgtcactg tcgctgcaac   26160
ctatgcaccc cgcaccgctc cctggttttgc aattcgcagc tgcttaacga aagtcaaatt   26220
atcggtacct ttgagctgca gggtccctcg cctgacgaaa agtccgcggc tccggggttg   26280
aaactcactc cggggctgtg gacgtcggct taccttcgca aatttgtacc tgaggactac   26340
cacgcccacg agattaggtt ctacgaagac caatcccgcc cgcctaatgc ggagcttacc   26400
gcctgcgtca ttacccaggg ccacattctt ggccaattgc aagccatcaa caaagcccgc   26460
caagagtttc tgctacgaaa gggacggggg gtttacttgg accccagtc cggcgaggag   26520
```

```
ctcaacccaa tcccccgcc gccgcagccc tatcagcagc agccgcgggc ccttgcttcc   26580
caggatggca cccaaaaaga agctgcagct gccgccgcca cccacggacg aggaggaata   26640
ctgggacagt caggcagagg aggttttgga cgaggaggag gaggacatga tggaagactg   26700
ggagagccta gacgaggaag cttccgaggt cgaagaggtg tcagacgaaa caccgtcacc   26760
ctcggtcgca ttcccctcgc cggcgcccca gaaatcggca accggttcca gcatggctac   26820
aacctccgct cctcaggcgc cgccggcact gcccgttcgc cgacccaacc gtagatggga   26880
caccactgga accagggccg gtaagtccaa gcagccgccg ccgttagccc aagagcaaca   26940
acagcgccaa ggctaccgct catggcgcgg gcacaagaac gccatagttg cttgcttgca   27000
agactgtggg ggcaacatct ccttcgcccg ccgctttctt ctctaccatc acggcgtggc   27060 cttccccgt aacatcctgc attactaccg tcatctctac agcccatact gcaccggcgg   27120
cagcggcagc aacagcagcg gccacacaga agcaaaggcg accggatagc aagactctga   27180
caaagcccaa gaaatccaca gcggcggcag cagcaggagg aggagcgctg cgtctggcgc   27240
ccaacgaacc cgtatcgacc cgcgagctta gaaacaggat ttttcccact ctgtatgcta   27300
tatttcaaca gagcaggggc caagaacaag agctgaaaat aaaaaacagg tctctgcgat   27360
ccctcacccg cagctgcctg tatcacaaaa gcgaagatca gcttcggcgc acgctggaag   27420
acgcggaggc tctcttcagt aaatactgcg cgctgactct taaggactag tttcgcgccc   27480
tttctcaaat ttaagcgcga aaactacgtc atctccagcg gccacacccg gcgccagcac   27540
ctgttgtcag cgccattatg agcaaggaaa ttcccacgcc ctacatgtgg agttaccagc   27600
cacaaatggg acttgcggct ggagctgccc aagactactc aacccgaata aactacatga   27660
gcgcgggacc ccacatgata tcccgggtca acggaatacg cgcccaccga aaccgaattc   27720
tcctggaaca ggcggctatt accaccacac ctcgtaataa ccttaatccc cgtagttggc   27780
ccgctgccct ggtgtaccag gaaagtcccg ctcccaccac tgtggtactt cccagagacg   27840
cccaggccga agttcagatg actaactcag ggcgcagct tgcgggcggc tttcgtcaca   27900
gggtgcggtc gcccgggcag ggtataactc acctgacaat cagagggcga ggtattcagc   27960
tcaacgacga gtcggtgagc tcctcgcttg gtctccgtcc ggacgggaca tttcagatcg   28020
gcggcgccgg ccgctcttca ttcacgcctc gtcaggcaat cctaactctg cagacctcgt   28080
cctctgagcc gcgctctgga ggcattggaa ctctgcaatt tattgaggag tttgtgccat   28140
cggtctactt taaccccttc tcgggacctc ccggccacta tccggatcaa tttattccta   28200
actttgacgc ggtaaaggac tcggcggacg gctacgactg aatgttaagt ggagaggcag   28260
agcaactgcg cctgaaacac ctggtccact gtcgccgcca caagtgcttt gcccgcgact   28320
ccggtgagtt ttgctacttt gaattgcccg aggatcatat cgagggcccg gcgcacggcg   28380
tccggcttac cgcccaggga gagcttgccc gtagcctgat tcgggagttt acccagcgcc   28440
ccctgctagt tgagcgggac aggggaccct gtgttctcac tgtgatttgc aactgtccta   28500
accctggatt acatcaagat ctttgttgcc atctctgtgc tgagtataat aaatacagaa   28560
attaaaatat actggggctc ctatcgccat cctgtaaacg ccaccgtctt cacccgccca   28620
agcaaaccaa ggcgaacctt acctggtact tttaacatct ctccctctgt gatttacaac   28680
agtttcaacc cagacggagt gagtctacga gagaacctct ccgagctcag ctactccatc   28740
agaaaaaaca ccacccctcct tacctgccgg gaacgtacga gtgcgtcacc ggccgctgca   28800
ccacacctac cgcctgaccg taaaccgac ttttccgga cagacctcaa taactctgtt   28860
taccagaaca ggaggtgagc ttagaaaacc cttagggtat taggccaaag gcgcagctac   28920
```

```
tgtggggttt atgaacaatt caagcaactc tacgggctat tctaattcag gtttctctag    28980
aaatggacgg aattattaca gagcagcgcc tgctagaaag acgcagggca gcggccgagc    29040
aacagcgcat gaatcaagag ctccaagaca tggttaactt gcaccagtgc aaaaggggta    29100
tcttttgtct ggtaaagcag gccaaagtca cctacgacag taataccacc ggacaccgcc    29160
ttagctacaa gttgccaacc aagcgtcaga aattggtggt catggtggga gaaaagccca    29220
ttaccataac tcagcactcg gtagaaaccg aaggctgcat tcactcacct tgtcaaggac    29280
ctgaggatct ctgcacccct attaagaccc tgtgcggtct caaagatctt attcccttta    29340
actaataaaa aaaaataata aagcatcact tacttaaaat cagttagcaa atttctgtcc    29400
agtttattca gcagcacctc cttgccctcc tcccagctct ggtattgcag cttcctcctg    29460
gctgcaaact ttctccacaa tctaaatgga atgtcagttt cctcctgttc ctgtccatcc    29520
gcacccacta tcttcatgtt gttgcagatg aagcgcgcaa gaccgtctga agataccttc    29580
aaccccgtgt atccatatga cacggaaacc ggtcctccaa ctgtgccttt tcttactcct    29640 cccttgtat  cccccaatgg gtttcaagag agtcccctg  gggtactctc tttgcgccta    29700
tccgaacctc tagttacctc caatggcatg cttgcgctca aaatgggcaa cggcctctct    29760
ctggacgagg ccggcaacct tacctcccaa aatgtaacca ctgtgagccc acctctcaaa    29820
aaaaccaagt caaacataaa cctggaaata tctgcacccc tcacagttac ctcagaagcc    29880
ctaactgtgg ctgccgccgc acctctaatg gtcgcgggca acacactcac catgcaatca    29940
caggccccgc taaccgtgca cgactccaaa cttagcattg ccacccaagg accccctcaca   30000 gtgtcagaag gaaagctagc cctgcaaaca tcaggccccc tcaccaccac cgatagcagt    30060
acccttacta tcactgcctc acccccctcta actactgcca ctggtagctt gggcattgac    30120
ttgaaagagc ccatttatac acaaaatgga aaactaggac taaagtacgg ggctcctttg    30180
catgtaacag acgacctaaa cactttgacc gtagcaactg gtccaggtgt gactattaat    30240
aatacttcct tgcaaactaa agttactgga gccttgggtt ttgattcaca aggcaatatg    30300
caacttaatg tagcaggagg actaaggatt gattctcaaa acagacgcct tatacttgat    30360
gttagttatc cgtttgatgc tcaaaaccaa ctaaatctaa gactaggaca gggccctctt    30420
tttataaact cagcccacaa cttggatatt aactacaaca aaggcctttta cttgtttaca    30480 gcttcaaaca attccaaaaa gcttgaggtt aacctaagca ctgccaaggg gttgatgttt    30540
gacgctacag ccatagccat taatgcagga gatgggcttg aatttggttc acctaatgca    30600
ccaaacacaa atcccctcaa aacaaaaatt ggccatggcc tagaatttga ttcaaacaag    30660
gctatggttc ctaaactagg aactggcctt agttttgaca gcacaggtgc cattacagta    30720
ggaaacaaaa ataatgataa gctaactttg tggaccacac cagctccatc tcctaactgt    30780
agactaaatg cagagaaaga tgctaaactc actttggtct taacaaaatg tggcagtcaa    30840
atacttgcta cagtttcagt tttggctgtt aaaggcagtt tggctccaat atctggaaca    30900
gttcaaagtg ctcatcttat tataagattt gacgaaaatg gagtgctact aaacaattcc    30960
ttcctggacc cagaatattg gaactttaga aatggagatc ttactgaagg cacagcctat    31020
acaaacgctg ttgatttat  gcctaaccta tcagcttatc caaaatctca cggtaaaact    31080
gccaaaagta acattgtcag tcaagtttac ttaaacggag acaaaactaa acctgtaaca    31140
ctaaccatta cactaaacgg tacacaggaa acaggagaca caactccaag tgcatactct    31200
atgtcatttt catgggactg gtctggccac aactacatta atgaaatatt tgccacatcc    31260
```

```
tcttacactt tttcatacat tgcccaagaa taaagaatcg tttgtgttat gtttcaacgt   31320
gtttattttt caattgcccg ggatcggtga tcaccgatcc agacatgata agatacattg   31380
atgagtttgg acaaaccaca actagaatgc agtgaaaaaa atgctttatt tgtgaaattt   31440
gtgatgctat tgctttattt gtaaccatta taagctgcaa taaacaagtt cccggatcgc   31500
gatccggccc gaggctgtag ccgacgatgg tgcgccagga gagttgttga ttcattgttt   31560
gcctccctgc tgcggttttt caccgaagtt catgccagtc cagcgttttt gcagcagaaa   31620
agccgccgac ttcggtttgc ggtcgcgagt gaagatccct ttcttgttac cgccaacgcg   31680
caatatgcct tgcgaggtcg caaaatcggc gaaattccat acctgttcac cgacgacggc   31740
gctgacgcga tcaaagacgc ggtgatacat atccagccat gcacactgat actcttcact   31800
ccacatgtcg gtgtacattg agtgcagccc ggctaacgta tccacgccgt attcggtgat   31860
gataatcggc tgatgcagtt tctcctgcca ggccagaagt tctttttcca gtaccttctc   31920
tgccgtttcc aaatcgccgc tttggacata ccatccgtaa taacggttca ggcacagcac   31980
atcaaagaga tcgctgatgg tatcggtgtg agcgtcgcag aacattacat tgacgcaggt   32040
gatcggacgc gtcgggtcga gtttacgcgt tgcttccgcc agtggcgcga aatattcccg   32100
tgcaccttgc ggacgggtat ccggttcgtt ggcaatactc cacatcacca cgcttgggtg   32160
gtttttgtca cgcgctatca gctctttaat cgcctgtaag tgcgcttgct gagtttcccc   32220
gttgactgcc tcttcgctgt acagttcttt cggcttgttg cccgcttcga aaccaatgcc   32280
taaagagagg ttaaagccga cagcagcagt ttcatcaatc accacgatgc catgttcatc   32340
tgcccagtcg agcatctctt cagcgtaagg gtaatgcgag gtacggtagg agttggcccc   32400
aatccagtcc attaatgcgt ggtcgtgcac catcagcacg ttatcgaatc ctttgccacg   32460
caagtccgca tcttcatgac gaccaaagcc agtaaagtag aacggtttgt ggttaatcag   32520
gaactgttcg cccttcactg ccactgaccg gatgccgacg cgaagcgggt agatatcaca   32580
ctctgtctgg cttttggctg tgacgcacag ttcatagaga taaccttcac ccggttgcca   32640
gaggtgcgga ttcaccactt gcaaagtccc gctagtgcct tgtccagttg caaccacctg   32700
ttgatccgca tcacgcagtt caacgctgac atcaccattg ccaccaccct gccagtcaac   32760
agacgcgtgg ttacagtctt gcgcgacatg cgtcaccacg gtgatatcgt ccacccaggt   32820
gttcggcgtg gtgtagagca ttacgctgcg atggattccg gcatagttaa agaaatcatg   32880
gaagtaagac tgcttttttct tgccgttttc gtcggtaatc accattcccg gcgggatagt   32940
ctgccagttc agttcgttgt tcacacaaac ggtgatacgt acactttttcc cggcaataac   33000 atacggcgtg acatcggctt caaatggcgt atagccgccc tgatgctcca tcacttcctg   33060
attattgacc cacactttgc cgtaatgagt gaccgcatcg aaacgcagca cgatacgctg   33120
gcctgcccaa ccttttcggta taaagacttc gcgctgatac cagacgttgc ccgcataatt   33180
acgaatatct gcatcggcga actgatcgtt aaaactgcct ggcacagcaa ttgcccggct   33240
ttcttgtaac gcgctttccc accaacgctg atcaattcca cagttttcgc gatccagact   33300
gaatgcccac aggccgtcga gttttttgat ttcacgggtt ggggtttcta caggacggac   33360
catgcgttcg accttttctct tctttttttgg gcccatgatg gcagatccgt atagtgagtc   33420
gtattagctg gttctttccg cctcagaagc catagagccc accgcatccc cagcatgcct   33480
gctattgtct tcccaatcct ccccccttgct gtcctgcccc accccacccc ccagaataga   33540
atgacaccta ctcagacaat gcgatgcaat ttcctcattt tattaggaaa ggacagtggg   33600
agtggcacct tccagggtca aggaaggcac gggggagggg caaacaacag atggctggca   33660
```

```
actagaaggc acagtcgagg ctgatcagcg agctctagat gcatgctcga gcggccgcca   33720
gtgtgatgga tatctgcaga attccagcac actggcggcc gttactagtg gatccgagct   33780
cggtacccgg ccgttataac accactcgac acggcaccag ctcaatcagt cacagtgtaa   33840
aaaagggcca agtgcagagc gagtatatat aggactaaaa aatgacgtaa cggttaaagt   33900
ccacaaaaaa cacccagaaa accgcacgcg aacctacgcc cagaaacgaa agccaaaaaa   33960
cccacaactt cctcaaatcg tcacttccgt tttcccacgt tacgtcactt cccattttaa   34020
gaaaactaca attcccaaca catacaagtt actccgccct aaaacctacg tcacccgccc   34080
cgttcccacg ccccgcgcca cgtcacaaac tccacccct cattatcata ttggcttcaa   34140
tccaaaataa ggtatattat tgatgatg                                      34168
```

ADENOVIRAL VECTOR ENCODING HUMAN ATONAL HOMOLOG-1 (HATH1)

CROSS-REFERENCE TO RELATED APPLICATIONS

This patent application is a divisional of U.S. application Ser. No. 14/879,318, filed Oct. 9, 2015, which claims the benefit of U.S. Provisional Patent Application No. 62/061,748, filed Oct. 9, 2014, which is incorporated by reference.

STATEMENT INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 49,283 Byte ASCII (Text) file named "738676_ST25.txt" created on Mar. 23, 2018.

BACKGROUND OF THE INVENTION

A majority of the world's population likely will experience some reduction in hearing capacity or a balance disorder in their lifetime. Approximately 17 percent (36 million) of American adults report some degree of hearing loss, and about 2-3 out of every 1,000 children in the United States are born deaf or hard-of-hearing (statistics from the National Institute on Deafness and Other Communication Disorders (NIDCD)).

In both hearing and balance, mechanical stimuli are translated into neural signals by sensory hair cells, damage to which is responsible for many types of hearing loss and balance disorders. Mechanical damage by, for example, loud noises, bends cochlear hair cells to the point that the hair cell can no longer transduce signals to the auditory nerves. As mammalian hair cells do not regenerate naturally, permanent hearing loss can occur if hair cells are damaged. Aside from acoustic trauma, which is the predominant cause of hearing impairment, hearing loss also can be caused by hereditary syndromes, bacterial or viral infections, use of prescription drugs, and presbycusis (hearing loss associated with old age). Likewise, balance disorders, especially vestibular disorders, can be caused by infection, head injury, pharmaceutical use, and age.

The most common treatments for hearing loss involve hearing aids and cochlear implants. Approximately 188,000 people worldwide have received cochlear implants, which includes roughly 41,599 adults and 25,500 children in the United States (NIDCD statistics). Treatment options for balance disorders include balance retraining, anti-vertigo or anti-nausea medications, and vestibular rehabilitation therapy. Such therapies, however, likely will be required over extended periods of time if the disorder is progressive, and many therapies for balance disorders do not provide permanent relief from dizziness. Currently, there are no effective pharmaceutical treatments for disorders involving loss or damage of sensory hair cells in the ear.

Thus, there remains a need for agents which can ameliorate disorders associated with destruction or loss of sensory hair cells, such as hearing loss and balance disorders. This invention provides such an agent.

BRIEF SUMMARY OF THE INVENTION

The invention provides an adenoviral vector comprising a serotype 5 adenoviral genome, except that two base pairs are deleted in the VA RNA I region, one or more endogenous nucleotides of the E1 region are deleted to render an endogenous gene in the E1 region functionally deficient, one or more endogenous nucleotides of the E3 region are deleted, and one or more endogenous nucleotides of the E4 region are deleted to render an endogenous gene in the E4 region functionally deficient, wherein a right side inverted terminal repeat (ITR), an E4 region polyadenylation sequence, and an E4 region promoter are retained, (b) an SV40 early polyadenylation sequence, (c) a nucleic acid sequence encoding a human atonal homolog-1 (Hath1) protein comprising SEQ ID NO: 1, (d) a human glial fibrillary acidic protein (GFAP) promoter, and (e) a transcriptionally inert spacer (TIS). Elements (b), (c), and (d) are located in sequence from 3' to 5' relative to the adenoviral genome in the E1 region of the adenoviral genome, and element (e) is located in the E4 region of the adenoviral genome between the E4 polyadenylation sequence and the E4 promoter.

The invention also provides a composition and method utilizing the aforementioned adenoviral vector to generate sensory cells in the inner ear of a human.

DETAILED DESCRIPTION OF THE INVENTION

Figure 1:
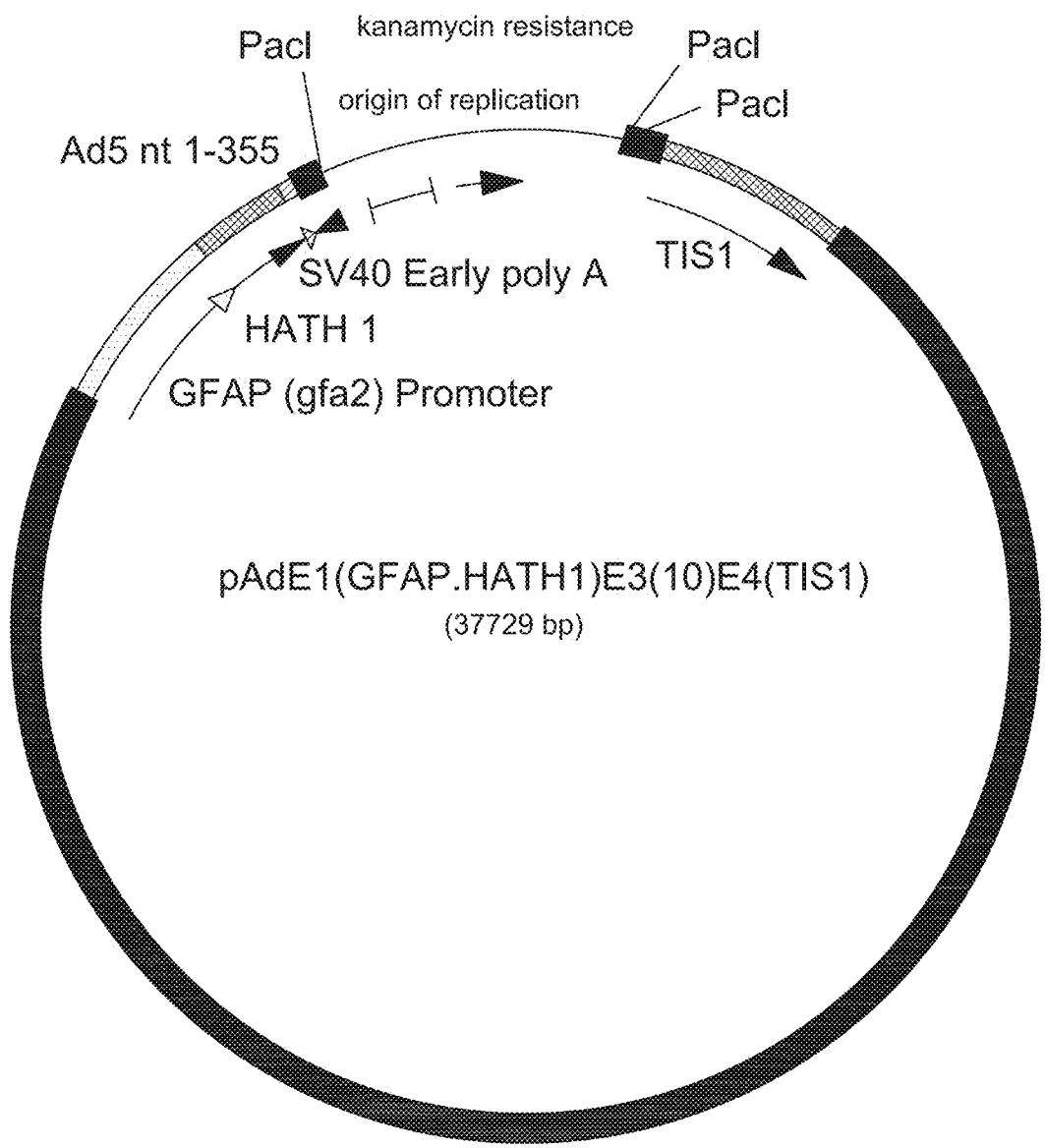
FIG. 1 is a schematic map of the plasmid pAdE1 (GFAP.Hath1)E3(10)E4(TIS1).

The invention is predicated, at least in part, on the discovery that sensory hair cells can be generated by delivering to the inner ear a serotype 5 adenoviral vector which comprises a nucleic acid sequence encoding a human atonal homolog-1 (Hath1) protein.

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence into the adenovirus.

The source of the viral genome for the adenoviral vector is a human serotype 5 adenovirus. Human adenovirus is classified as subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), or an unclassified serogroup (e.g., serotypes 49 and 51). Adenoviral serotypes 1 through 51 (i.e., Ad1 through Ad51) are available from the American Type Culture Collection (ATCC, Manassas, Va.).

The inventive adenoviral vector is replication-deficient. A replication-deficient adenoviral vector requires complementation of one or more gene functions or regions of the adenoviral genome that are required for replication, as a result of, for example, a deficiency in one or more replication-essential gene function or regions, such that the adenoviral vector does not replicate in typical host cells, especially those in a human to be infected by the adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part, thereby rendering the gene or genomic region "functionally deficient." Deletion of an entire gene region often is not required for disruption of a replication-essential gene function. However, for the purpose of providing sufficient space in the adenoviral genome for one or more transgenes, removal of a majority of one or more gene regions may be desirable. In this respect, the adenoviral vector desirably comprises an adenoviral genome, except that one or more endogenous nucleotides of one or more replication-essential genes or genomic regions are deleted to render an endogenous gene or genomic region functionally deficient. While deletion of genetic material is preferred, mutation of genetic material also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

The replication-deficient adenoviral vector preferably retains at least a portion of the adenoviral genome. The adenoviral vector can comprise any portion of the adenoviral genome, including protein coding and non-protein coding regions. The adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions). Alternatively, the adenoviral vector can comprise non-protein coding regions of the adenoviral genome, including, for example one or more promoters, transcription termination sequences, or polyadenylation sequences of early region or late region genes, or one or more inverted terminal repeat (ITR) sequences. In one embodiment, the inventive adenoviral vector retains at least a right side inverted terminal repeat (ITR), an E4 region polyadenylation sequence, and an E4 region promoter.

The replication-deficient adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the functionally deficient replication-essential gene functions. Such complementation can be effected in any suitable manner, for example, by using complementing cells and/or exogenous DNA (e.g., helper adenovirus) encoding the disrupted replication-essential gene functions.

The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad)). See Morsy et al., *Proc. Natl. Acad. Sci. USA*, 95: 965-976 (1998); Chen et al., *Proc. Natl. Acad. Sci. USA*, 94: 1645-1650 (1997); and Kochanek et al., *Hum. Gene Ther.*, 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenoviral vector to propagate (e.g., to form adenoviral vector particles).

The E3 region does not include any replication-essential gene functions, such that a deletion of the E3 region in part or in whole does not require complementation of any gene functions in the E3 region for the adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region may be deleted in whole or in part, or retained in whole or in part. The size of the deletion may be tailored so as to retain an adenoviral vector whose genome closely matches the optimum genome packaging size. A larger deletion will accommodate the insertion of larger heterologous nucleic acid sequences in the adenoviral genome. In one embodiment of the invention, the L4 polyadenylation signal sequences, which reside in the E3 region, are retained.

The E4 region comprises multiple open reading frames (ORFs) that encode multiple endogenous genes. An adenoviral vector with a deletion of all of the open reading frames of the E4 region except ORF6, and in some cases ORF3, does not require complementation of any gene functions in the E4 region for the adenoviral vector to propagate (e.g., to form adenoviral vector particles). Conversely, an adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenoviral vector to propagate (e.g., to form adenoviral vector particles).

The late regions of the adenoviral genome include the L1, L2, L3, L4, and L5 regions. The adenoviral vector also can have a mutation in the major late promoter (MLP), as discussed in International Patent Application Publication WO 2000/000628, which can render the adenoviral vector replication-deficient if desired.

Preferably, the one or more regions of the adenoviral genome that contain one or more deficiencies in replication-essential gene functions desirably are one or more early regions of the adenoviral genome, i.e., the E1, E2, and/or E4 regions, optionally with a deletion in part or in whole of the E3 region.

In one embodiment, one or more endogenous nucleotides of the E1 region and the E4 region are deleted in the inventive adenoviral vector to render an endogenous gene in the E1 region functionally deficient and an endogenous gene in the E4 region functionally deficient (denoted an E1/E4-deficient adenoviral vector). The inventive adenoviral vector can comprise a deletion in at least one replication-essential gene function of the E1 region of the adenoviral genome, and preferably comprises a deletion of all of the replication-essential gene functions of the E1 region. In this respect, the deletion of the E1 region of the inventive adenoviral vector can comprise deletion of the promoters and coding regions of the E1A and E1B endogenous genes. The deletion of the E4 region desirably comprises at least one replication-essential gene function of the E4 region, and preferably comprises a deletion of all of the replication-essential gene functions of the E4 region. In this respect, the deletion of the E4 region of the inventive adenoviral vector can comprise deletion of all of the endogenous genes of the E4 region. In addition to the deletion of the E1 region and the E4 region of the adenoviral genome, one or more endogenous nucleotides of the E3 region can be deleted in the inventive adenoviral vector, and preferably the inventive adenoviral vector comprises a deletion of at least one gene function of the nonessential E3 region of the adenoviral genome (denoted an E1/E3/E4-deficient adenoviral vector). In addition to deletions of the E1, E3, and E4 regions of the serotype 5 adenoviral genome, the inventive adenoviral vector also desirably comprises a deletion in one of the virus-associated RNAs (e.g., VA-RNA-1 and/or VA-RNA-2). Preferably, the inventive adenoviral vector comprises a deletion in the VA-RNA-I region. The deletion of the VA-RNA-I region can be of any suitable size, but desirably is from 1 to 10 base pairs, preferably from 1 to 5 base pairs, and most preferably from 1 to 3 base pairs, or a range defined by any two of the foregoing values. In one embodiment, two base pairs are deleted in the VA RNA I region of the adenoviral vector.

In a preferred embodiment, the genome of the inventive serotype 5 adenoviral vector comprises a deletion of E1 region nucleotides 356-3510, inclusive, a deletion of E3 region nucleotides 28,593-30,471, inclusive, a deletion of E4 region nucleotides 32,827-35,563, and a deletion of VA-RNA-1 region nucleotides 10,594 and 10595. However, other deletions may be appropriate. For example nucleotides 356-3329 or 356-3510 can be removed to create a deficiency in replication-essential E1 gene functions, and nucleotides 28,594-30,469 can be deleted from the E3 region of the adenoviral genome.

The inventive adenoviral vector comprises a transcriptionally inert spacer (TIS). The transcriptionally inert spacer sequence provides growth of a multiply replication-deficient adenoviral vector (e.g., an E1/E4-deficient adenoviral vector) in a complementing cell line similar to that achieved by an adenoviral vector deficient in a single replication-essential gene function (e.g., an E1-deficient adenoviral vector). The TIS sequence can contain any nucleotide sequence or sequences which are of a desired length, such as sequences at least about 15 nucleotides (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The TIS sequence can be coding or non-coding and native or non-native with respect to the adenoviral genome, but does not restore the replication-essential function to the deficient region. The TIS also can contain an expression cassette.

In one embodiment, the transcriptionally inert spacer comprises a polyadenylation sequence and/or a gene that is non-native with respect to the adenoviral vector. The spacer element can comprise any suitable polyadenylation sequence, such as, for example, the polyadenylation sequences of bovine growth hormone (BGH), polyoma virus, thymidine kinase (TK), Epstein Barr Virus (EBV), human papillomavirus (HPV) and bovine papillomavirus (BPV). Preferably, the TIS sequence comprises a simian virus-40 (SV40) polyadenylation sequence. Examples of suitable non-native genes for inclusion in the TIS include, but are not limited to, nucleic acid sequences encoding marker proteins such as pGUS, secretory alkaline phosphatase, luciferase, β-galactosidase, and human anti-trypsin; therapeutic factors; potential immune modifiers such as B3-19K, E3-14.7, ICP47, fas ligand, and CTLA4; biologically inactive sequences (e.g., sequences that are (i) not transcribed to produce a product or (ii) encode a defective or biologically inactive product); and other innocuous sequences (e.g., the β-glucuronidase gene).

Preferably, the TIS comprises in sequence from 5' to 3' relative to the adenoviral genome (i) a polyadenylation (poly(A)) sequence and transcription termination sequence from simian virus 40 (SV40), (ii) a nucleic acid sequence encoding a β-glucuronidase gene, and (iii) a polyadenylation (poly(A)) sequence and transcription termination sequence from the bovine growth hormone (BGH) gene. The use of a transcriptionally inert spacer in an adenoviral vector is further described in, for example, U.S. Pat. No. 5,851,806 and International Patent Application Publication WO 1997/021826.

By removing all or part of the adenoviral genome, for example, one or more endogenous nucleotides of the E1, E3, and E4 regions of the adenoviral genome, the resulting adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of the adenoviral vector particle. The exogenous nucleic acid sequence preferably is positioned in the E1 region, the E3 region, or the E4 region of the adenoviral genome.

The replication-deficient adenoviral vector of the invention can be produced in complementing cell lines that provide gene functions not present in the replication-deficient adenoviral vector, but required for viral propagation, at appropriate levels in order to generate high titers of viral vector stock. Such complementing cell lines are known and include, but are not limited to, 293 cells (described in, e.g., Graham et al., J. Gen. Virol., 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.*, 71: 9206-9213 (1997)). Other suitable complementing cell lines include cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenoviral vector. Alternatively, the inventive adenoviral vector can comprise a non-native replication-essential gene that complements for the one or more replication-essential gene functions lacking in the inventive replication-deficient adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenoviral vector, or an adenovirus of a different species than the inventive adenoviral vector).

The inventive adenoviral vector comprises a nucleic acid sequence encoding a human atonal homolog-1 (Hath1) protein. Hath1 is an atonal-associated factor. Atonal-associated factors are transcription factors of the basic helix-loop-helix (bHLH) family of proteins that transdifferentiate supporting cells into sensory hair cells in the ear. The basic domain of the protein is responsible for DNA binding and protein function. Atonal-associated factors are found in a variety of animals and insects, including mice (mouse atonal homolog-1 (Math1)), chickens (chicken atonal homolog-1 (Cath1)), *Xenopus* (*Xenopus* atonal homolog-1 (Xath1)), and humans (human atonal homolog-1 (Hath1)). Atonal-associated proteins like Math1 and Hath1 have been shown to be essential for hair cell development and can stimulate hair cell regeneration in the ear (see, e.g., Groves et al., *Annu. Rev. Neurosci.*, 36: 361-381 (2013)). Hath1 is further characterized in, for example, Ben-Arie et al., *Human Molecular Genetics*, 5, 1207-1216 (1996); and Mulvaney, J. and Dabdoub, A, *J. Assoc. Res. Otolaryngol.*, 13(3): 281-289 (2012), and atonal-associated factors are generally described in International Patent Application WO 00/73764.

Hath1 nucleic acid and amino acid sequences are publicly available as, for example, GenBank Accession Nos. U61148 (GI No. 1575354) and AAB41305.1 (GI No. 1575355), respectively. Preferably, the inventive adenoviral vector comprises a nucleic acid sequence comprising SEQ ID NO: 1, which encodes a Hath1 protein.

While the nucleic acid sequence encoding a Hath1 protein comprises SEQ ID NO: 1, many modifications and variations (e.g., mutation) of the nucleic acid sequence are possible and appropriate in the context of the invention. It is believed that the function of atonal-associated factors is dependent on the helix-loop-helix (HLH) portion of the protein, particularly the basic region of the HLH domain (Chien et al., *Proc. Natl. Acad. Sci.*, 93, 13239-13244 (1996)). Accordingly, any modification of the nucleic acid sequence encoding the Hath1 protein desirably is located outside of the basic domain of the protein such that the function of the Hath1 protein is retained or enhanced.

In addition to the nucleic acid sequence encoding a Hath1 protein, the inventive adenoviral vector preferably comprises expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and are described in, for example, Goeddel, *Gene Expression Technology: Methods in Enzymology*, Vol. 185, Academic Press, San Diego, Calif. (1990). Ideally, the Hath1-encoding nucleic acid sequence is operably linked to a promoter and a polyadenylation sequence. The promoter desirably is a tissue-specific promoter, i.e., a promoter that is preferentially activated in a given tissue and results in expression of a gene product in the tissue where activated. A tissue specific promoter for use in the inventive adenoviral vector can be chosen based upon the target tissue or cell-type in which the Hath1-encoding nucleic acid sequence is to be expressed. Preferred tissue-specific promoters for use in the inventive adenoviral vector are specific to supporting cells or sensory hair cells. Tissue specific promoters specifically activated in hair cells include, for example, an atonal promoter or a myosin VIIa promoter. Tissue specific promoters specifically activated in supporting cells include, for example, a hes-1 promoter and a human glial fibrillary acidic protein (GFAP) promoter. In a preferred embodiment, the promoter is a human GFAP promoter comprising SEQ ID NO: 2. The human GFAP protein is a soluble structural protein expressed primarily in astrocytes of the central nervous system, non-myelin forming Schwann cells, and other select cell types. Within the anatomy of the inner ear, GFAP expression is primarily restricted to the supporting cells of the sensory organs (i.e. the Deiter's cells and phalangeal cells of the organ of Corti, those located within the canal ampullae, and supporting cells of the extrastriolar regions in the utricle/saccule maculae).

Other examples of tissue-specific promoters that could be used in the invention include the BRN.3C promoter, the BRN 3.1 promoter, the POU ORF3 factor promoter, the BRK1 promoter, the BRK3 promoter, the chordin promoter, the noggin promoter, the jagged1 promoter, the jagged2 promoter, and the notch1 promoter.

To optimize protein production, the Hath1-encoding nucleic acid sequence further comprises a polyadenylation sequence downstream of the Hath1 coding sequence. Any suitable polyadenylation sequence can be used, including a synthetic optimized sequence, as well as the polyadenylation sequence of bovine growth hormone (BGH), polyoma virus, thymidine kinase (TK), Epstein Barr Virus (EBV), human papillomavirus (HPV) and bovine papillomavirus (BPV). The polyadenylation sequence preferably is a simian virus-40 (SV40) early polyadenylation sequence, which is the polyadenylation sequence for the SV40 early RNA products (see, e.g., Carswell, S. and Alwine, J. C., *Mol. Cell. Biol.*, 9(10): 4248-4258 (1989)). In addition to the promoter and polyadenylation sequence, the nucleic acid sequence encoding Hath1 desirably comprises all of the proper transcription signals (and translation signals, where appropriate) correctly arranged such that the nucleic acid sequence is properly expressed in the cells into which it is introduced. If desired, the nucleic acid sequence also can incorporate splice sites (i.e., splice acceptor and splice donor sites) to facilitate mRNA production.

The tissue-specific promoter, the nucleic acid sequence encoding a Hath1 protein, and the SV40 early polyadenylation sequence can be positioned within the inventive adenoviral vector in any suitable orientation, so long as production of the adenoviral vector is not impeded and the Hath1-encoding nucleic acid sequence is efficiently expressed in host cells. In general, the promoter will be positioned upstream of the Hath1-encoding nucleic acid sequence, and the SV40 early polyadenylation sequence will be positioned downstream of the Hath1-encoding nucleic acid sequence. In one embodiment, the adenoviral vector can comprise the aforementioned elements in sequence from 5' to 3' relative to the adenoviral genome: a tissue specific promoter (e.g., a human GFAP promoter), the nucleic acid sequence encoding a Hath1 protein, and the SV40 early polyadenylation sequence. Alternatively, the adenoviral vector can comprise the aforementioned elements in sequence from 3' to 5' relative to the adenoviral genome: the SV40 early polyadenylation sequence, the nucleic acid sequence encoding a Hath1 protein, and a tissue specific promoter (e.g., a human GFAP promoter). The nucleic acid sequence encoding a Hath1 protein, as well as the tissue-specific promoter and SV40 early poly(a) sequence operatively linked thereto, can be inserted at any position in the adenoviral genome so long as insertion in the position allows for the formation of the adenoviral vector particle. Preferably, the Hath1-encoding nucleic acid sequence is positioned in the E1 region or the E4 region of the adenoviral genome. In a preferred embodiment, the E1 region of the adenoviral genome is replaced with the SV40 early polyadenylation sequence, the nucleic acid sequence encoding a Hath1 protein, and a human GFAP promoter in sequence from 3' to 5' relative to the adenoviral genome.

The inventive adenoviral vector can comprise the nucleic acid sequence of, for example, SEQ ID NO: 3.

The invention provides a composition comprising the adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenoviral vector. Any suitable carrier can be used within the context of the invention, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenoviral vector is part of a composition formulated to protect the adenoviral vector from damage prior to administration. For example, the composition can be formulated to reduce loss of the adenoviral vector on devices used to prepare, store, or administer the adenoviral vector, such as glassware, syringes, or needles. The composition can be formulated to decrease the light sensitivity and/or temperature sensitivity of the adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenoviral vector, and facilitate its administration. Formulations for adenoviral vector-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the adenoviral vector can be present in a composition with other therapeutic or biologically-active agents. For example, factors that control inflammation, such as ibuprofen or steroids, can be part of the composition to reduce swelling and inflammation associated with in vivo administration of the adenoviral vector. Antibiotics, i.e., microbicides and fungicides, can be present to treat existing infection and/or reduce the risk of future infection, such as infection associated with gene transfer procedures.

The invention also provides a method of generating sensory cells in the inner ear of a human in need thereof. The method comprises administering a composition comprising the inventive adenoviral vector described herein, whereupon the nucleic acid sequence encoding the Hath1 protein is expressed and sensory cells in the inner ear are generated. As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering to the human a "therapeutically effective amount" of the composition. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the inventive adenoviral vector to elicit a desired response in the individual. For example, a therapeutically effective amount of the composition of the invention is an amount which results in expression of the Hath1 protein at levels that treats hearing loss or a balance disorder in a human.

Alternatively, the pharmacologic and/or physiologic effect may be prophylactic, i.e., the effect completely or partially prevents a disease or symptom thereof. In this respect, the inventive method comprises administering a "prophylactically effective amount" of the composition comprising the inventive adenoviral vector. A "prophylactically effective amount" refers to an amount effective, at dosages and for periods of time necessary, to achieve a desired prophylactic result (e.g., prevention of disease onset). Therapeutic or prophylactic efficacy can be monitored by periodic assessment of treated patients.

Suitable doses and dosage regimens can be determined by conventional range-finding techniques known to those of ordinary skill in the art. Desirably, a single dose of adenoviral vector comprises about $1\times10^5$ or more particles (which also are referred to as particle units (pu)) of the adenoviral vector, e.g., about $1\times10^6$ or more particles, about $1\times10^7$ or more particles, about $1\times10^8$ or more particles, about $1\times10^9$ or more particles, or about $3\times10^8$ or more particles of the adenoviral vector. Alternatively, or in addition, a single dose of adenoviral vector comprises about $3\times10^{14}$ particles or less of the adenoviral vector, e.g., about $1\times10^{13}$ particles or less, about $1\times10^{12}$ particles or less, about $3\times10^{11}$ particles or less, about $1\times10^{11}$ particles or less, about $1\times10^{10}$ particles or less, or about $1\times10^{9}$ particles or less of the adenoviral vector. Thus, a single dose of adenoviral vector can comprise a quantity of particles of the adenoviral vector in a range defined by any two of the aforementioned values. For example, a single dose of adenoviral vector can comprise $1\times10^{5}$-$1\times10^{14}$ particles, $1\times10^{7}$-$1\times10^{12}$ particles, $1\times10^{8}$-$1\times10^{11}$ particles, $3\times10^{8}$-$3\times10^{11}$ particles, $1\times10^{9}$-$1\times10^{12}$ particles, $1\times10^{9}$-$1\times10^{11}$ particles, $1\times10^{9}$-$1\times10^{10}$ particles, or $1\times10^{10}$-$1\times10^{12}$ particles, of the adenoviral vector. In other words, a single dose of adenoviral vector can comprise, for example, about $1\times10^{6}$ pu, $2\times10^{6}$ pu, $4\times10^{6}$ pu, $1\times10^{7}$ pu, $2\times10^{7}$ pu, $4\times10^{7}$ pu, $1\times10^{8}$ pu, $2\times10^{8}$ pu, $3\times10^{8}$ pu, $4\times10^{8}$ pu, $1\times10^{9}$ pu, $2\times10^{9}$ pu, $3\times10^{9}$ pu, $4\times10^{9}$ pu, $1\times10^{10}$ pu, $2\times10^{10}$ pu, $3\times10^{10}$ pu, $4\times10^{10}$ pu, $1\times10^{11}$ pu, $2\times10^{11}$ pu, $3\times10^{11}$ pu, $4\times10^{11}$ pu, $1\times10^{12}$ pu, $2\times10^{12}$ pu, $3\times10^{12}$ pu, or $4\times10^{12}$ pu of the adenoviral vector. Of course, other routes of administration may require smaller or larger doses to achieve a therapeutic effect. Any necessary variations in dosages and routes of administration can be determined by the ordinarily skilled artisan using routine techniques known in the art.

The interior space of the structures of the inner ear is limited. The volume of pharmaceutical composition administered directly into the inner ear structures should be carefully monitored, as forcing too much composition will damage the sensory epithelium. For a human patient, the volume administered is preferably about 1 μl to about 500 μl (e.g., from about 10 μl to about 400 μl) of composition. For example, from about 10 μl to about 200 μl (e.g., about 15 μl, 20 μl, 30 μl, 40 μl, 50 μl, 60 μl, 70 μl, 80 μl, 90 μl, 100 μl, 125 μl, 150 μl, 175 μl, or a range defined by any two of the foregoing values) of composition can be administered. In one embodiment, the entire fluid contents of the inner ear structure, e.g., the cochlea or semi-circular canals, is replaced with pharmaceutical composition. In another embodiment, a pharmaceutical composition comprising the expression vector of the inventive method is slowly released into the inner ear structure, such that mechanical trauma is minimized.

In one embodiment of the inventive method, the composition comprising the Hath1-encoding adenoviral vector desirably is administered only once to the inner ear of the human during a given treatment period. In other words, the inventive method comprises administration of a single dose of the inventive adenoviral vector to the inner ear of a human. In other embodiments, it may be advantageous to administer the composition two or more (i.e., multiple) times to the inner ear of the human. Thus, the invention provides administration of two or more doses of the inventive adenoviral vector to the inner ear of a human. For example, the composition comprising the inventive adenoviral vector can be administered at least twice to the same ear. When the composition is administered multiple times to the inner ear of a human, each administration can be separated by days, weeks, months, or even years depending on the response of the human to the first and subsequent administrations of the composition. For example, the multiple administrations can be separated by about 1 week to about 4 weeks (e.g., 2 or 3 weeks), or by about 30 days to about 90 days (e.g., about 40 days, about 50 days, about 60 days, about 70 days, about 80 days, or a range defined by any two of the foregoing values). However, multiple administrations of the composition (e.g., 3, 4, 5, 6, or more administrations) can be separated by any suitable number of days (e.g., 2, 7, 10, 14, 21, 28, 35, 42, 49, 56, 63, 70, 77, 85 or more days between doses), months (e.g., 1, 3, 6, or 9 months between doses), or years (e.g., 1, 2, 3, 4, 5 or more years between doses) so long as the nucleic acid sequence encoding the Hath1 protein is sufficiently expressed and sensory cells in the inner ear are generated.

The composition desirably is administered to a human to treat a disorder associated with loss, damage, or absence of sensory hair cells in the inner ear, such as hearing loss and balance disorders. In this respect, the composition can be administered to a human suffering from hearing loss or a balance disorder, or a human suffering from both hearing loss and a balance disorder. Hearing loss can be caused by damage of hair cells of the organ of Corti due to bacterial or viral infection, heredity, physical injury, acoustic trauma, and the like. While hearing loss is easily identified, balance disorders manifest in a broad variety of complications easily attributable to other ailments. Symptoms of a balance disorder include disorientation, dizziness, vertigo, nausea, blurred vision, clumsiness, and frequent falls. Balance disorders treated by the inventive method preferably involve a peripheral vestibular disorder (i.e., a disturbance in the vestibular apparatus) involving dysfunctional translation of mechanical stimuli into neural impulses due to damage or lack of sensory hair cells.

The composition can be administered to the inner ear of a human using any suitable method known in the art. No matter the route of administration, the inventive adenoviral vector must reach the sensory epithelium of the inner ear. The most direct routes of administration, therefore, entail surgical procedures which allow access to the interior of the structures of the inner ear. Inoculation via cochleostomy allows administration of the expression vector directly to the regions of the inner ear associated with hearing. Cochleostomy involves drilling a hole through the cochlear wall, e.g., in the otic capsule below the stapedial artery as described in Kawamoto et al., *Molecular Therapy*, 4(6), 575-585 (2001), and release of the composition comprising the adenoviral vector. Administration to the endolymphatic compartment is particularly useful for administering the composition to the areas of the inner ear responsible for hearing. Alternatively, the composition can be administered to the semicircular canals via canalostomy. Canalostomy provides for transgene expression in the vestibular system and the cochlea, whereas cochleostomy does not provide as efficient transduction in the vestibular space. The risk of damage to cochlear function is reduced using canalostomy in as much as direct injection into the cochlear space can result in mechanical damage to hair cells (Kawamoto et al., supra). Administration procedures also can be performed under fluid (e.g., artificial perilymph), which can comprise factors to alleviate side effects of treatment or the administration procedure, such as apoptosis inhibitors or anti-inflammatories.

Another direct route of administration to the inner ear is through the round window, either by injection or topical application to the round window. Administration via the round window is especially preferred for delivering an adenoviral vector to the perilymphatic space. Transgene expression in cochlear and vestibular neurons and cochlear sensory epithelia has been observed following administration of expression vectors via the round window (Staecker et al., *Acta Otolaryngol*, 121, 157-163 (2001)). In certain cases, it may be appropriate to administer multiple applications and/or employ multiple routes, e.g., canalostomy and cochleostomy, to ensure sufficient exposure of supporting cells to the adenoviral vector. A particularly preferred method for delivery of the inventive composition to the inner ear is described in, e.g., U.S. Pat. No. 7,387,614.

The composition comprising the inventive adenoviral vector can be present in or on a device that allows controlled or sustained release of the adenoviral vector, such as a sponge, meshwork, mechanical reservoir or pump, or mechanical implant. For example, a biocompatible sponge or gelform soaked in the composition comprising the adenoviral vector can be placed adjacent to the round window, through which the expression vector permeates to reach the cochlea (as described in Jero et al., *Hum. Gene Ther.*, 12: 539-548 (2001)). In another embodiment, mini-osmotic pumps can be used to provide sustained release of the adenoviral vector over extended periods of time (e.g., five to seven days), allowing small volumes of composition comprising the adenoviral vector to be administered, which can prevent mechanical damage to endogenous sensory cells. The composition also can be administered in the form of sustained-release formulations (see, e.g., U.S. Pat. No. 5,378,475) comprising, for example, gelatin, chondroitin sulfate, a polyphosphoester, such as bis-2-hydroxyethyl-terephthalate (BHET), or a polylactic-glycolic acid.

While not preferred, the composition comprising the inventive adenoviral vector can be administered parenterally, intramuscularly, intravenously, or intraperitoneally. If parenterally administered to a patient, the adenoviral vector desirably is specifically targeted to sensory epithelial cells, such as supporting cells. For example, the adenoviral vector can be targeted to scarred sensory epithelium to promote generation of exogenous hair cells to replace damaged endogenous hair cells. An adenoviral vector can be modified to alter the binding specificity or recognition of an expression vector for a receptor on a potential host cell by deleting regions of the fiber, penton, or hexon, inserting various native or non-native ligands into portions of the coat protein, and the like. One of ordinary skill in the art will appreciate that parenteral administration can require large doses or multiple administrations to effectively deliver the expression vector to the appropriate host cells.

The inventive method can be part of a treatment regimen involving other therapeutic modalities. For example, the inventive method can be performed on a human that has been treated, is being treated, or will be treated with one or more drugs or surgery. In addition, the inventive method can be used in conjunction with proliferation agents that induce proliferation of supporting cells in the inner ear, such as vascular endothelial growth factors (VEGF), fibroblast growth factors (FGFs), epidermal growth factor (EGF), E2F, and cell cycle up-regulators. The inventive method also can be performed in conjunction with the implantation of hearing devices, such as cochlear implants.

Sensory cell (e.g., hair cell) generation in the inner ear can be determined using a variety of means known in the art. For example, sensory hair cells can be detected via scanning electron microscopy or via detection of myosin VIIa, which is a hair cell-specific protein detected by immunochemistry. However, the mere presence of sensory hair cells does not necessarily imply a functional system for recognizing environmental stimuli. Functional sensory cells must be operably linked to neural pathways, such that mechanical stimuli are translated to nerve impulses recognized by the brain. Accordingly, while detection of hair cell generation is appropriate for determining successful expression of the Hath1-encoding nucleic acid sequence to target tissue, the generation of sensory cells preferably leads to an improvement in sensory perception by the human subject. In this respect, examination of subject awareness is an indicator of changes in sensory perception.

A change in the ability of a subject to detect sound can be assessed through administration of simple hearing tests, such as a tone test commonly administered by an audiologist. In most mammals, a reaction to different frequencies indicates a change in sensory perception. In humans, comprehension of language also is appropriate. For example, it is possible for a subject to hear while being unable to understand speech. A change in sensory perception is indicated by the ability to distinguish different types of acoustic stimuli, such as differentiating language from background noise, and by understanding speech. Speech threshold and discrimination tests are useful for such evaluations.

Evaluation of changes in balance, motion awareness, and/or timing of response to motion stimuli also can be achieved using a variety of techniques. Vestibular function can be measured by comparing the magnitude of response to motion stimulus (gain) or timing of initiation of response (phase). Animals can be tested for Vestibulo-Ocular Reflex (VOR) gain and phase using scleral search coils to evaluate improvements in sensory perception. Electronystagmography (ENG) records eye movements in response to stimuli such as, for instance, moving or flashing lights, body repositioning, fluid movement inside the semicircular canals, and the like. Evaluation of balance during movement using a rotating chair or moving platform also is useful in this respect.

The following examples further illustrate the invention but, of course, should not be construed as in any way limiting its scope.

Example 1

This example demonstrates a method of generating the inventive serotype 5 adenoviral vector.

An adenovirus vector comprising a serotype 5 adenoviral genome with a deletion of the E1, E3, and E4 regions and encoding the Hath1 protein was constructed using the ADFAST™ protocol described in, e.g., U.S. Pat. No. 6,475,757. Using the ADFAST™ procedure, a plasmid was constructed that encodes an entire serotype 5 adenovirus vector genome. Isolation of a single genetic clone of the final vector genome was achieved by two sequential colony-growth steps in bacteria. This AdFAST™ plasmid was converted to a viral vector upon introduction into mammalian cells that complement for adenovirus vector growth. Subsequent expansion via serial passaging was then performed to generate adenovirus vector stocks. The steps to construct the Hath1-expressing serotype 5 adenoviral vector are summarized below.

Construction of Plasmids

A plasmid denoted pAd3511gfa2.HATH1.sv was digested with restriction enzymes to gel extract a GFAP.HATH1 expression cassette. A base plasmid comprising a serotype 5 adenoviral genome with deletions in the E1, E3, and E4 regions and a transcriptionally inert spacer containing an SV40 poly(A) and transcription termination sequences, a β-glucuronidase gene, and a bovine growth hormone gene (BGH) poly(A) and transcription termination sequences (denoted pAdE1 (BN) E3 (10) E4 (TIS1)) was linearized and purified. The pAdE1 (BN) E3 (10) E4 (TIS1) plasmid was homologously recombined with the GFAP.HATH1 expression cassette in *E. coli*, resulting in the plasmid pAdE1(GFAP.Hath1)E3(10)E4(TIS1).

To ensure clonality of the full length adenovirus vector plasmid, an aliquot of pAdE1(GFAP.Hath1)E3(10)E4(TIS1) ADFAST™ plasmid DNA was used to transform DH10B *E. coli* by limiting serial dilutions. Well-defined and isolated colonies were selected from the highest dilution plate containing the fewest colonies. Miniprep plasmid DNA was prepared and digested with Hind III+SpeI to confirm plasmid integrity via RFLP analysis. Positive corresponding miniprep DNA was used to generate another series of limiting dilutions, which were then used to transform DH10B *E. coli*. An aliquot of liquid culture from a single colony on the plate containing the fewest colonies was used to generate miniprep DNA, whereupon ApaI was used to further confirm plasmid integrity. Remaining liquid culture of the positive clone was used to streak an LB-kanamycin plate. A single bacterial transformant was expanded for preparation of EndoFree ADFAST™ plasmid DNA by the HISPEED™ Plasmid Maxi Kit (Qiagen, Venlo, The Netherlands) following the manufacturer's protocol. The resulting plasmid preparation was confirmed by BglI, EcoRV, HindIII, KpnI, and BamHI+PacI restriction endonuclease digestion. A map of the pAdE1(GFAP.Hath1)E3(10)E4 (TIS1) is shown in FIG. 1. The DNA sequence of pAdE1 (GFAP.Hath1)E3(10)E4(TIS1) was then determined.

Vector Conversion

18 μg of the endotoxin-free pAdE1(GFAP.HATH1)E3(10) E4(TIS1) was digested in 300 μL with Pac I restriction endonuclease and purified by Phenol Chloroform Isoamylalcohol (PCI). Briefly, 100 uL of PCI was added to the restriction reaction, mixed by vigorous inversion, spun at 13,000 RPM for two minutes in a microfuge, and the upper aqueous phase was transferred to a new tube. The DNA was precipitated by the addition of 30 μL (0.1 volume) of 5M NaCl and 800 μL of absolute ethanol, incubated on ice for 10 minutes, and then spun in a microfuge at 13,000 RPM for 10 minutes, and the supernatant was decanted. The pellet was washed with 500 μL of 70% ethanol, centrifuged and decanted as above, and the DNA pellet air-dried. The DNA was resuspended in 30 μL TE and the DNA concentration was determined by absorbance at 260 nm. 293-ORF6 cells were transfected with 4 μg of the Pac I-digested and -purified DNA using POLYFECT™ reagent (Qiagen, Venlo, The Netherlands), and incubated at 37° C., 5% $CO_2$, for three days. The transfection lysate (generated by three freeze-thaw cycles) was used to initiate serial passaging to generate high titer lysate. After confirmation by PCR, the high titer lysate was used to expand the AdGFAP.HATH1.11D adenovector.

Construction of the AdGFAP.HATH1.11D Adenoviral Vector

Figure 2:
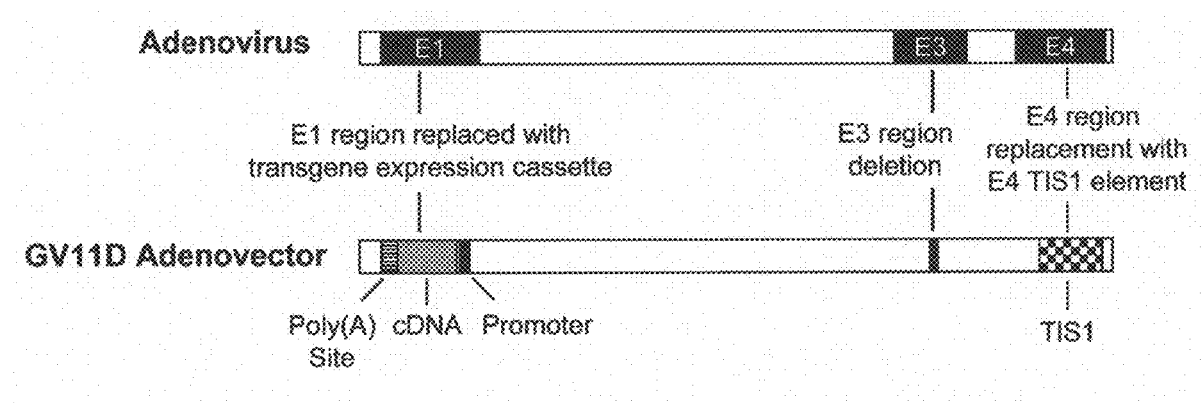
FIG. 2 is a schematic map of the adenoviral vector AdGFAP.HATH1.11D.

To construct the adenoviral vector AdGFAP.HATH1.11D, also referred to as GV501A (a map of which is shown in FIG. 2), the ADFAST™ plasmid pAdE1(GFAP.HATH1)E3 (10)E4(TIS1) was digested with the restriction endonuclease PacI and transfected into 293-ORF6 cells using standard procedures. The adenovector lysate from the transfected cells was serially passaged five times to expand the titer and volume of the AdGFAP.HATH1.11D/GV501A lysate and produce a high titer (HT2) stock. The 293-ORF6 cells used for the GV501A transfection and construction were maintained in a limited access cell culture room to ensure separation from other activities. In addition, the transfection, serial passaging, and production of the AdGFAP.HATH1.11D/GV501A vector were conducted in a separate virus culture room under procedures to maintain separation and limited access. The identity and integrity of the AdGFAP.HATH1.11D/GV501A vector was confirmed by PCR analysis at the HT2 passage. The HT2 lysate was then used to generate adenovector stock expansions.

Hath1 Transgene Expression Assays

The AdGFAP.HATH1.11D vector was certified for functional transgene expression based on HATH1-driven sensory cell regeneration in a mouse utricle model. Results of this experiment showed that the AdGFAP.HATH1.11D vector was capable of inducing sensory cell regeneration, and therefore produced functional HATH1 protein. In addition, AdGFAP.HATH1.11D was tested for expression of Hath1 transgene mRNA using a modified Hath1 mRNA expression assay. The assay involved infecting 293 cells with AdGFAP.HATH1.11D and isolating total RNA 24 hours post-infection. Hath1-specific mRNA expression was measured by a semi-quantitative RT-PCR method. The results of this assay showed evidence of Hath1 expression based on the RNA/DNA- and DNA-only primers and probes observed.

The results of this example confirm the generation of a serotype 5 adenoviral vector in which one or more endogenous nucleotides of the E1 region and the E4 region have been deleted, and which comprises an SV40 early polyadenylation sequence, a Hath1-encoding nucleic acid sequence operably linked to a human GFAP promoter, and a transcriptionally inert spacer (TIS).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of generating sensory cells in the inner ear of a human in need thereof, which method comprises administering to the inner ear of the human a composition comprising an adenoviral vector and a pharmaceutically acceptable carrier, wherein the adenoviral vector comprises a nucleic acid sequence comprising SEQ ID NO: 3, wherein SEQ ID NO: 3 comprises the nucleic acid sequence of SEQ ID NO: 1 encoding human atonal homolog-1 (Hath1) protein and whereupon SEQ ID NO: 1 is expressed and sensory cells in the inner ear are generated.

2. A method of generating sensory cells in the inner ear of a human in need thereof, which method comprises administering to the inner ear of the human a composition comprising an adenoviral vector and a pharmaceutically acceptable carrier, wherein the adenoviral vector comprises a nucleic acid sequence consisting of SEQ ID NO: 3, wherein SEQ ID NO: 3 comprises the nucleic acid sequence of SEQ ID NO: 1 encoding human atonal homolog-1(Hath1) protein and whereupon SEQ ID NO: 1 is expressed and sensory cells in the inner ear are generated.

3. The method of claim 1, wherein the composition comprises between $1\times10^{10}$ and $1\times10^{13}$ particles of the adenoviral vector per milliliter.

4. The method of claim 2, wherein the composition comprises between $1\times10^{10}$ and $1\times10^{13}$ particles of the adenoviral vector per milliliter.

5. The method of claim 1, wherein the human in need thereof is a human suffering from hearing loss.

6. The method of claim 2, wherein the human in need thereof is a human suffering from hearing loss.

7. The method of claim 1, wherein the human in need thereof is a human suffering from a balance disorder.

8. The method of claim 2, wherein the human in need thereof is a human suffering from a balance disorder.

\* \* \* \* \*